(12) United States Patent
Zisapel et al.

(10) Patent No.: US 8,461,297 B2
(45) Date of Patent: Jun. 11, 2013

(54) CYTOPLASMIC MALATE DEHYDROGENASE (MDH1) TARGETED TREATMENT FOR NEURODEGENERATIVE DISEASES

(75) Inventors: Nava Zisapel, Tel Aviv (IL); Yael Mali, Ramat Gan (IL)

(73) Assignee: Ramot at Tel-Aviv University, Ltd., Tel-Aviv (IL)

( * ) Notice: Subject to any disclaimer, the term of this patent is extended or adjusted under 35 U.S.C. 154(b) by 278 days.

(21) Appl. No.: 12/682,120

(22) PCT Filed: Oct. 12, 2008

(86) PCT No.: PCT/IL2008/001351
§ 371 (c)(1),
(2), (4) Date: Apr. 14, 2010

(87) PCT Pub. No.: WO2009/047770
PCT Pub. Date: Apr. 16, 2009

(65) Prior Publication Data
US 2010/0279943 A1    Nov. 4, 2010

Related U.S. Application Data

(60) Provisional application No. 60/979,080, filed on Oct. 11, 2007, provisional application No. 61/078,401, filed on Jul. 6, 2008.

(51) Int. Cl.
*A61K 38/00* (2006.01)
*C12P 21/06* (2006.01)

(52) U.S. Cl.
USPC ............................ 530/326; 530/300; 435/69.1

(58) Field of Classification Search
None
See application file for complete search history.

(56) References Cited

U.S. PATENT DOCUMENTS 6,274,138 B1    8/2001   Bandman
7,834,146 B2 *  11/2010  Kovalic et al. ................ 530/350

FOREIGN PATENT DOCUMENTS

EP    1754485 B2    2/2007
WO   2006/066244 B1  6/2006

OTHER PUBLICATIONS

Setoyama et al., J. Mol. Biol. 1988, 202, 355-64.*
Adam-Vizi, Vera (2005) Production of Reactive Oxygen Species in Brain Mitochondria: Contribution by Electron Transport Chain and Non-Electron Transport Chain Sources Antioxid Redox Signal. 7(9-10):1140-1149.
Barron, John T. et al., (1998) Malate-Aspartate Shuttle, Cytoplasmic NADH Redox Potential, and Energetics in Vascular Smooth Muscle. J Mol Cell Cardiol 30(8):1571-1579.
Beal, M. Flint (2000) Mitochondria and the pathogenesis of ALS. Brain 123(7):1291-1292.
Bendotti, Caterina and Carri, Maria Teresa (2004) Lessons from models of SOD1-linked familial ALS. Trends Mol Med. 10(8):393-400.
Brockington, Alice et al., (2006) Expression of vascular endothelial growth factor and its receptors in the central nervous system in amyotrophic lateral sclerosis. J Neuropathol Exp Neurol. 65(1):26-36.
Bruijin, Lucie I. et al., (2004) Unraveling the mechanisms involved in motor neuron degeneration in ALS. Annu Rev Neurosci. 27:723-749.
Bubis, M. and Zisapel, N. (1998) A role for NAD+and cADP-ribose in melatonin signal transduction. Mol Cell Endocrinol 137(1):59-67.
Butterworth, Roger F. and Besnard, Anne-Marie (1990) Thiamine-dependent enzyme changes in temporal cortex of patients with Alzheimer's disease. Metab Brain Dis. 5(4):179-184.
Carri, Maria Teresa et al., (1997) Expression of a Cu, Zn superoxide dismutase typical of familial amyotrophic lateral sclerosis induces mitochondrial alteration and increase of cytosolic Ca2+concentration in transfected neuroblastoma SH-SY5Y cells. FEBS Lett 414(2):365-368.
Cashman, N. R. et al., (1992) Neuroblastoma x spinal cord (NSC) hybrid cell lines resemble developing motor neurons. Dev Dyn 194(3):209-221.
Chan, Francis Ka-Ming (2004) Monitoring molecular interactions in living cells using flow cytometric analysis of fluorescence resonance energy transfer. Methods Mol Biol 261:371-382.
Fergani, Anissa et al., (2007) Increased peripheral lipid clearance in an animal model of amyotrophic lateral sclerosis. J Lipid Res 48(7):1571-80.
Greenway, Matthew J. et al., (2006) ANG mutations segregate with familial and 'sporadic' amyotrophic lateral sclerosis. Nat Genet 38(4):411-413.
Hu, R. et al., (2007) Proteomic Analysis of Hypoxia-Induced Responses in the Syncytialization of Human Placental Cell Line BeWo. Placenta 28(5-6):399-407.
Hugon, J. et al., (1989) Glutamate dehydrogenase and aspartate aminotransferase in leukocytes of patients with motor neuron disease. Neurology 39(7):956-958.
Kaal, Evert C. A. et al., (2000) Chronic Mitochondrial Inhibition Induces Selective Motoneuron Death In Vitro: A New Model for Amyotrophic Lateral Sclerosis. J Neurochem 74(3):1158-1165.
Korolainen, Minna A. et al., (2006) Oxidative modification of proteins in the frontal cortex of Alzheimer's disease brain. Neurobiol Aging 27(1):42-53.
Kruman, Inna I. et al., (1999) ALS-Linked Cu/Zn-SOD Mutation Increases Vulnerability of Motor Neurons to Excitotoxicity by a Mechanism Involving Increased Oxidative Stress and Perturbed Calcium Homeostasis. Exp Neurol 160(1):28-39.

(Continued)

*Primary Examiner* — Olga N Chernyshev
(74) *Attorney, Agent, or Firm* — Roach Brown McCarthy & Gruber, P.C.; Kevin D. McCarthy

(57) ABSTRACT

The present invention provides compositions for treating neurodegenerative diseases, including ALS, involving complex formation of cytosolic malate dehydrogenase with certain neurodegenerative disease-causing proteins, comprising an agent capable of reducing an interaction between a malate dehydrogenase protein and a conformationally altered or mutant protein associated with a neurodegenerative disorder, including mutant SOD1 protein. The present invention also provides methods of identifying an agent capable of treating such disorders, including ALS, comprising testing agents for the ability to disrupt or prevent formation of a malate dehydrogenase complex with a conformationally altered or mutant protein associated with a neurodegenerative disorder, including MDH-mutant-SOD1 complex, and methods of treating neurodegenerative disorders.

2 Claims, 17 Drawing Sheets

OTHER PUBLICATIONS

Lambrechts, Diether et al., (2003) VEGF is a modifier of amyotrophic lateral sclerosis in mice and humans and protects motoneurons against ischemic death. Nat Genet 34(4):383-394.

Lederer, C. W. et al., (2007) Pathways and genes differentially expressed in the motor cortex of patients with sporadic amyotrophic lateral sclerosis. BMC Genomics 8:26.

Mali, Yael and Zisapels, Nava (2008) Gain of interaction of ALS-linked G93A superoxide dismutase with cytosolic malate dehydrogenase. Neurobiology of Disease 32(1):133-141.

Marxsen, J. H. et al., (2004) Hypoxia-inducible factor-1 (HIF-1) promotes its degradation by induction of HIF-alpha-prolyl-4-hydroxylases. Biochem J 381(3):761-767.

McKenna, Mary C. et al., (2006) Neuronal and astrocytic shuttle mechanisms for cytosolic-mitochondrial transfer of reducing equivalents: Current evidence and pharmacological tools. Biochem Pharmacol 71(4):399-407.

Menzies, Fiona M. et al., (2002) Mitochondrial dysfunction in a cell culture model of familial amyotrophic lateral sclerosis. Brain 125(7):1522-1533.

Miulli, Dan E. et al., (1993) Plasma concentrations of glutamate and its metabolites in patients with Alzheimer's disease. J Am Osteopath Assoc 93(6)670-676.

Op Dev Velde, W. And Stam, F. C. (1976) Some cerebral proteins and enzyme systems in Alzheimer's presenile and senile dementia. J Am Geriatr Soc 24(1):12-16.

Palaiologos, Georgios et al., (1988) Evidence that aspartate aminotransferase activity and ketodicarboxylate carrier function are essential for biosynthesis of transmitter glutamate. J Neurochem 5(1):317-320.

Pan, Y. et al., (2007) Multiple factors affecting cellular redox status and energy metabolism modulate hypoxia-inducible factor prolyl hydroxylase activity in vivo and in vitro. Mol Cell Biol 27(3):912-925. Epub Nov. 13, 2006.

Plaitakis, Andreas et al., (1988) The neuroexcitotoxic amino acids glutamate and aspartate are altered in the spinal cord and brain in amyotrophic lateral sclerosis. Ann Neurol 24(3):446-449.

Ramos, Milagros et al., (2003) Developmental changes in the Ca2+-regulated mitochondrial aspartate-glutamate carrier aralar1 in brain and prominent expression in the spinal cord. Brain Res Dev Brain Res 143(1):33-46.

Rizzardini, Milena et al., (2005) Low levels of ALS-linked Cu/Zn superoxide dismutase increase the production of reactive oxygen species and cause mitochondrial damage and death in motor neuron-like cells. J Neurol Sci 232(1-2):95-103.

Sheu, Kuan Fu et al., (1985) An immunochemical study of the pyruvate dehydrogenase deficit in Alzheimer's disease brain. Ann Neurol 17(5):444-449.

Shinder, Gayle A. et al., (2001) Mutant Cu/Zn-superoxide dismutase proteins have altered solubility and interact with heat shock/stress proteins in models of amyotrophic lateral sclerosis. J Biol Chem 276(16):12791-12796.

Sicilliano, G. et al., (2007) Antioxidant capacity and protein oxidation in cerebrospinal fluid of amyotrophic lateral sclerosis. J Neurol 254(5):575-580.

Takeuchi, Hideyuki et al.,(2002) Mitochondrial localization of mutant superoxide dismutase 1 triggers caspase-dependent cell death in a cellular model of familial amyotrophic lateral sclerosis. J Biol Chem 277(52):50966-50972.

Van Westerlaak, M. G. H. et al., (2001) Differential cortico-motoneuron vulnerability after chronic mitochondrial inhibition in vitro and the role of glutamate receptors. Brain Res 922(2):243-249.

Zhang, Fujian et al.,(2007) Interaction between familial amyotrophic lateral sclerosis (ALS)-linked SOD1 mutants and the dynein complex. J Biol Chem 282(22):16691-9.

Zheng, J. et al., (2003) Disruption of an intersubunit interaction underlies Ca2+-calmodulin modulation of cyclic nucleotide-gated channels. J Neurosci 23(22):8167-8175.

Zhou, Lufang et al., (2005) Regulation of lactate production at the onset of ischaemia is independent of mitochondrial NADH/NAD+: insights from in silico studies. J Physiol 569(3):925-937.

ISR of PCT/IL2008/001351.

IPRP of PCT/IL2008/001351.

* cited by examiner

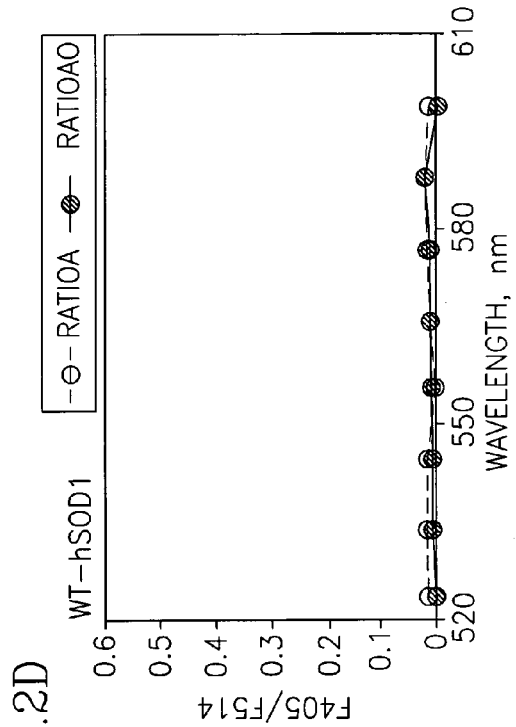
FIG.2B
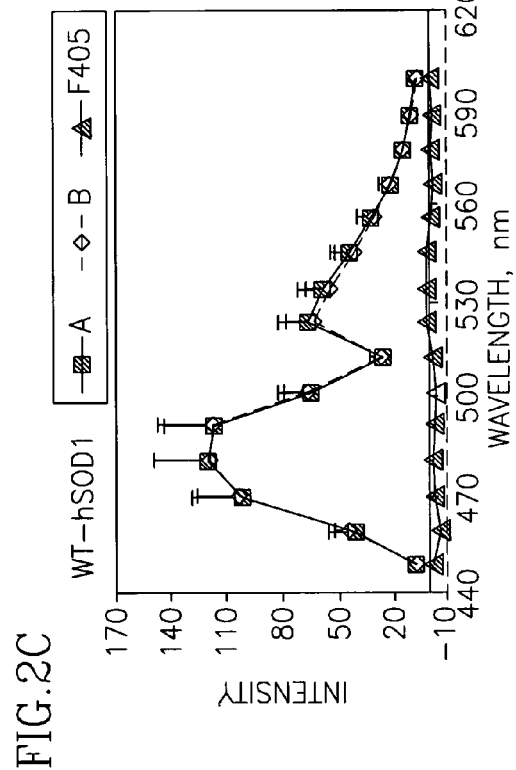
FIG.2D
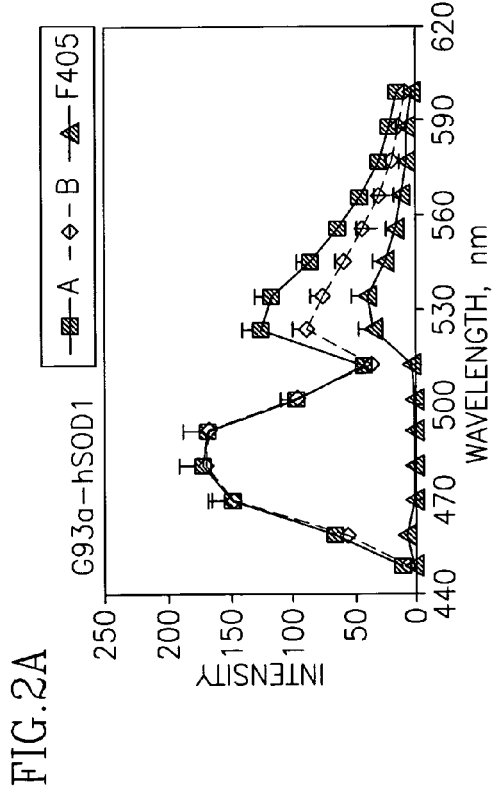
FIG.2A
FIG.2C

CYTOPLASMIC MALATE DEHYDROGENASE (MDH1) TARGETED TREATMENT FOR NEURODEGENERATIVE DISEASES

REFERENCE TO CO-PENDING APPLICATIONS

Priority is claimed as a U.S. national entry under 35 U.S.C. 371 of PCT/IL2008/001351, filed on Oct. 12, 2008; which claims priority from U.S. provisional patent application No. 60/979,080, filed on Oct. 11, 2007 and U.S. provisional patent application No. 61/078,401, filed on Jul. 6, 2008.

FIELD OF THE INVENTION

The present invention relates to agents including peptides and small molecules capable of preventing interactions between cytoplasmic malate dehydrogenase and disease causing proteins, useful in the treatment of neurodegenerative disorders and methods of screening thereof.

BACKGROUND

Amyotrophic lateral sclerosis (ALS) is an adult-onset, fatal motor-neuron neurodegenerative disease. The molecular pathways leading to motor neuron injury and cell death in ALS are incompletely understood. In about 3% of ALS cases, the disease is caused by mutations in the gene encoding the human copper-zinc superoxide dismutase (hSOD1) gene. More than 90 ALS-related mutations in the hSOD1 gene have been identified in familial ALS. These suggested toxic gain of function rather than loss of catalytic hSOD1 activity as the cause of ALS, but the nature of the toxicity has not been determined. Mitochondrial dysfunction and excessive production of reactive oxygen species (ROS) have repeatedly been demonstrated in cells expressing the mutant G93A-hSOD1, an example of such mutations (1-4). These changes mirror alterations in mitochondrial electron transport chain (ETC) activities observed in ALS patients (3,5,6).

Malate dehydrogenases (MDH, L-malate:NAD oxidoreductase, IUBMB Enzyme Nomenclature EC 1.1.1.37) play an important role in mitochondrial respiration. Specifically, they catalyze the NAD/NADH-dependent interconversion of malate and oxaloacetate in the cytoplasm (cytMDH) and mitochondria (MitMDH). This reaction plays a key part in the malate/aspartate shuttle between the cytoplasm across the mitochondrial membrane, and in the tricarboxylic acid cycle within the mitochondrial matrix.

Previous studies have indicated normal or increased malate dehydrogenase (MDH) activity in other neurodegenerative disorders such as Alzheimer's Disease (AD) [Butterworth and Besnard, *Metab Brain Dis* 1990:5; 179-184, Miulli et al. *J Am Osteopath Assoc* 1993:93; 670-676, den Velde and Stam, *J Am Geriatr Soc* 1976:24; 12-16, Sheu et al. *Ann Neurol* 1985:17; 444-449]. Korolainen et al. [*Neurobiol Aging*. 2006:27;42-53] discloses increased amounts of mitochondrial glutamate dehydrogenase and cytosolic malate dehydrogenase in AD brains. Furthermore, Korolainen teach that these two enzymes exhibit a significantly decreased degree of oxidation in AD brains compared to controls. [Korolainen et al. *Neurobiol Aging*. 2006:27;42-53].

A role of MDH in neurodegenerative disease etiology has not been described until now. Rather, changes in MDH activity were considered to be the outcome and not the cause of neurodegeneration. For example, Ferraiuolo et al [Journal of Neuroscience, 2007, 27(34):9201-9219] teaches that amongst the myriad of up-regulated genes, malate dehydrogenase is also upregulated during ALS as detected by microarray analysis. None of the above references disclose or suggest the presence of a MDH complex with a neurodegenerative disease-causing protein or its utility as a therapeutic target for ALS or any neurodegenerative diseases.

SUMMARY OF THE INVENTION

The present invention provides compositions and methods of treating ALS and neurodegenerative disorders in a subject, comprising an agent capable of reducing or inhibiting an interaction between a malate dehydrogenase (MDH) protein and a neurodegenerative disease causing protein such as an SOD1 mutant protein. The present invention also provides methods of identifying an agent capable of treating ALS, comprising testing candidate agents for the ability to disrupt or prevent formation of a malate dehydrogenase complex with a conformationally altered or mutant neurodegenerative disease-causing protein.

The present invention is based in part on the unexpected finding that a cytoplasmic enzyme, malate dehydrogenase, forms a complex with specific mutant proteins associated with neurodegenerative processes. The present invention is exemplified by specific MDH1-derived peptides comprising the interacting motif that compete with MDH1 for the interaction site.

In one aspect, the present invention provides a method of treating ALS in a subject in need thereof, the method comprising administering to the subject a therapeutically effective amount of an agent capable of reducing an interaction between malate dehydrogenase and an SOD1 protein, thereby treating ALS. In one embodiment, the target SOD1 protein is a mutant SOD1 protein. In another embodiment, the mutant SOD1 protein is associated with amyotrophic lateral sclerosis (ALS). In another embodiment, the agent is a peptide. In a specific embodiment, the agent is a peptide derived from the sequence of a MDH protein. Each possibility represents a separate embodiment of the present invention.

In another aspect, the present invention provides a method of treating a neurodegenerative disorder, the method comprising administering to an individual in need thereof a therapeutically effective amount of an agent capable of increasing brain mitochondrial respiration, thereby treating the neurodegenerative disorder, with the proviso that said agent is not pyruate or oxaloacetate. In one embodiment, the agent is capable of increasing cytoplasmic malate dehydrogenase activity in a subject in need thereof. In another embodiment, the agent is capable of increasing cytoplasmic malate levels in a subject in need thereof. In another embodiment, the agent is a peptide agent. In another embodiment, the peptide agent comprises at least 4-7 consecutive amino acids of human malate dehydrogenase. In another embodiment the peptide agent comprises at least 8-18 contiguous amino acids of human malate dehydrogenase. In another embodiment, the agent comprises the sequence set forth in SEQ ID NO: 1, corresponding to amino acids 217-239 of the cytMDH protein SWLKGEFITTVQQRGAAVIKARK (SEQ ID NO: 1). Each possibility represents a separate embodiment of the present invention.

The agent of methods and compositions of the present invention is, in certain embodiments, a peptide. In some embodiments, the peptide comprises a fragment of a malate dehydrogenase protein. In another embodiment, the malate dehydrogenase protein is a cytosolic malate dehydrogenase protein (cytMDH). In another embodiment, the malate dehydrogenase protein is a cytMDH malate dehydrogenase protein isoform. In another embodiment, the malate dehydrogenase protein is a human malate dehydrogenase protein. In another embodiment, the malate dehydrogenase protein is a human cytMDH protein isoform. In another embodiment, the malate dehydrogenase is any other malate dehydrogenase known in the art. Each possibility represents a separate embodiment of the present invention.

In another embodiment, the present invention provides a fragment of G93A-hSOD1 of 19-50 amino acids in length, the peptide comprising the sequence set forth in SEQ ID NO: 1. In another embodiment, the G93A-hSOD1 fragment is 19-45 amino acids in length. In another embodiment, the G93A-hSOD1 fragment is 19-40 amino acids in length. In another embodiment, the G93A-hSOD1 fragment is 19-35 amino acids in length. In another embodiment, the G93A-hSOD1 fragment is 19-30 amino acids in length. In another embodiment, the G93A-hSOD1 fragment is 19-25 amino acids in length. In another embodiment, the G93A-hSOD1 fragment is 25-45 amino acids in length. In another embodiment, the G93A-hSOD1 fragment is 25-40 amino acids in length. In another embodiment, the G93A-hSOD1 fragment is 25-35 amino acids in length. In another embodiment, the G93A-hSOD1 fragment is 25-30 amino acids in length. In another embodiment, a peptide of the present invention has the sequence set forth in SEQ ID NO: 1. Each possibility represents a separate embodiment of the present invention.

In another embodiment, the present invention provides a pharmaceutical composition comprising a pharmaceutically acceptable carrier and as an active ingredient, a peptide agent capable of preventing an interaction between malate dehydrogenase and a mutant SOD1 protein, wherein said mutant SOD1 protein is associated with an amyotrophic lateral sclerosis (ALS).

In another embodiment, the present invention provides a method of identifying an agent capable of treating ALS, the method comprising the steps of (a) contacting said agent with a preparation of a complex of a malate dehydrogenase protein and a mutant SOD1 protein, wherein said mutant SOD1 protein is associated with amyotrophic lateral sclerosis (ALS); and measuring an amount of the complex in the presence of the agent, whereby, if said amount of the complex in the presence of the agent is less than the initial amount, then said agent is capable of treating amyotrophic lateral sclerosis.

In another embodiment, the present invention provides a method of identifying an agent capable of treating ALS, the method comprising the steps of: (a) contacting a malate dehydrogenase protein with a mutant SOD1 protein, wherein the mutant SOD1 protein is associated with amyotrophic lateral sclerosis (ALS), in the presence of the agent; (b) measuring the amount of complex formation between the malate dehydrogenase protein and the mutant SOD1 protein, following step (a); c) contacting the malate dehydrogenase protein with the mutant SOD1 protein in the absence of the agent; and d) measuring the amount of complex formation between the malate dehydrogenase protein and the mutant SOD1 protein, following step (c), whereby, if the amount of step (b) is less than the amount of step (d), then the agent is capable of treating amyotrophic lateral sclerosis.

In another embodiment, a complex of the present invention is fluorescently labeled. In another embodiment, the step of measuring an amount of a malate dehydrogenase-mutant SOD1 complex is performed by measuring a signal from the complex. In another embodiment, the signal is fluorescence signal. In another embodiment, the signal is a FRET signal. In another embodiment, an alteration in the signal is measured following addition of the test agent. As described herein, the present invention provides methods readily generalizable by one skilled in the art to any type of quantitative or semi-quantitative signal that can be engineered depend on an intact malate dehydrogenase-mutant SOD1 complex. Each possibility represents a separate embodiment of the present invention.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2. A) Emission spectra obtained upon excitation at 405 nm of cells expressing G93A-hSOD1-CFP and YFP-tagged candidate protein (data set A). The FRET-related YFP emission (FIG. 2A—F405) was extracted by subtracting the CFP spectrum collected from control cells expressing the G93A-hSOD1-CFP alone (data set B). B) F405/F514 (RatioA) in cells expressing G93A-hSOD1-CFP and YFP-tagged candidate and F405/F514 caused by the direct excitation of YFP (RatioA0) in NSC-34 cells expressing only the YFP-tagged candidate protein. C) Emission spectra obtained upon excitation at 405 nm of cells expressing WT-hSOD1-CFP and YFP-tagged candidate protein (FIG. 2C, data set A). The FRET-related YFP emission (FIG. 2C—F405) was extracted by subtracting the CFP spectrum collected from control cells expressing the G93A-hSOD1-CFP alone (FIG. 2C, data set B). D) F405/F514 (RatioA) in cells expressing WT-hSOD1-CFP and YFP-tagged candidate and F405/F514 caused by the direct excitation of YFP (RatioA0) in NSC-34 cells expressing only the YFP-tagged candidate protein.

DESCRIPTION OF THE PREFERRED EMBODIMENTS

Figure 1A:
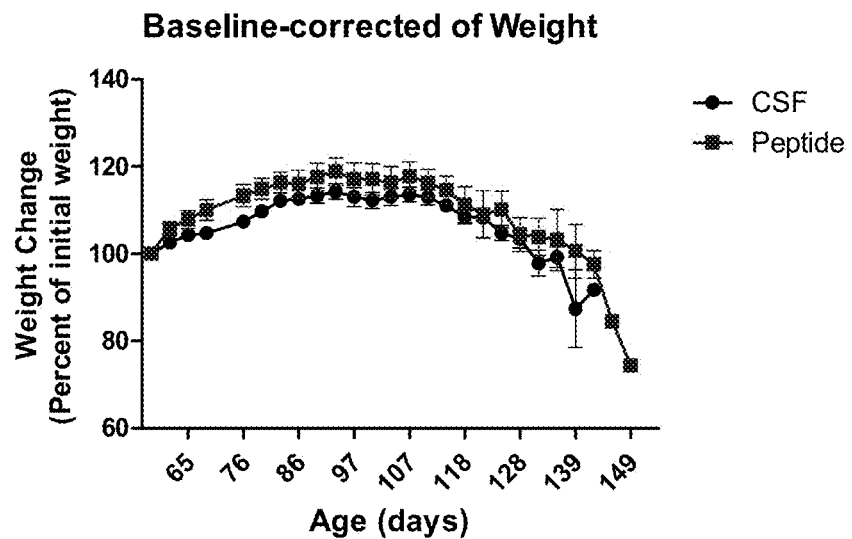
FIG. 1. FACS analysis of A) G93A-hSOD1-GFP expressing NSC-34 cells transfected with BFP-GFP chimera expression plasmid; B) NSC-34 cells transfected with BFP-GFP chimera expression plasmid; and C) G93A-hSOD1-GFP expressing NSC-34 cells transfected with BFP expression plasmid. Excitation-UV light; Emission—530 nm.
Figure 1B:
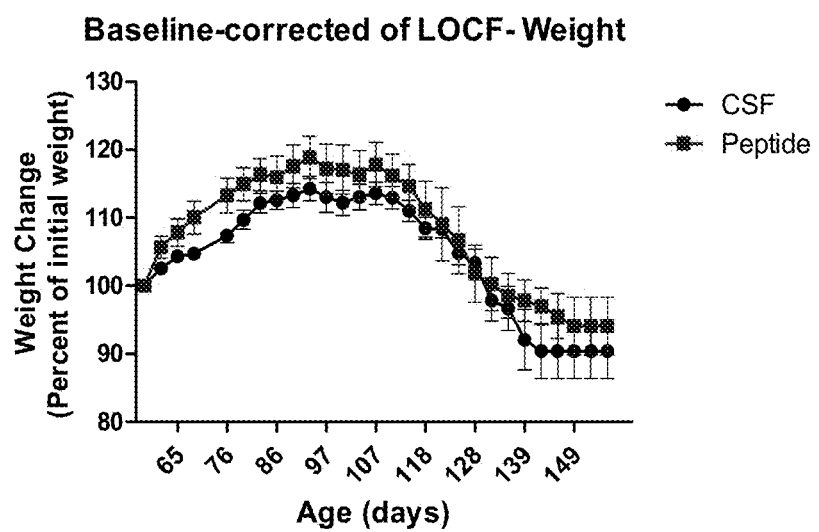
Figure 1C:
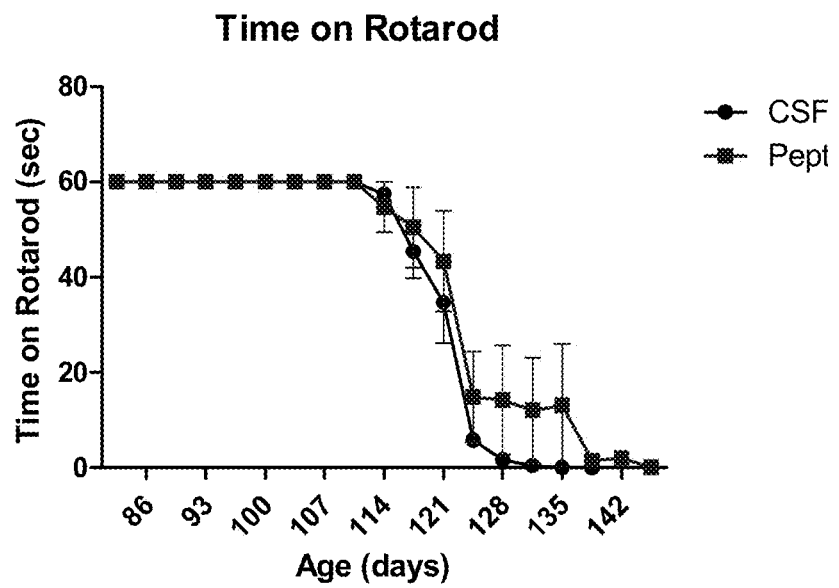
Figure 1D:
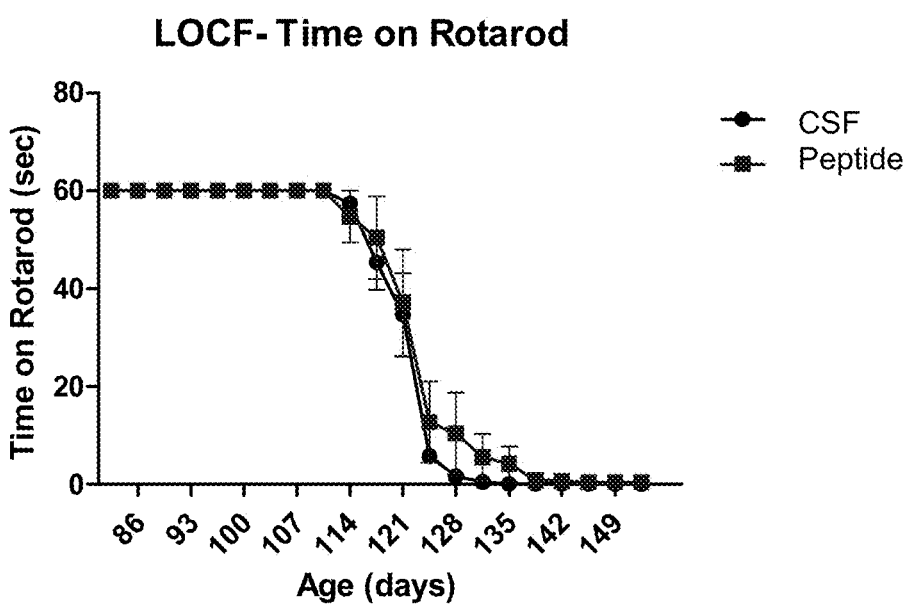

The present invention provides methods of treating neurodegenerative disorders such as ALS in a subject, comprising the step of administering to the subject an agent capable of reducing an interaction between a malate dehydrogenase protein and an SOD1 protein. The present invention also provides methods of identifying an agent capable of treating ALS, comprising testing agents for ability to disrupt or prevent formation of a malate dehydrogenase-SOD1 complex, and methods of treating neurodegenerative disorders that are caused by complex formation of other a conformationally altered or mutant neurodegenerative disease-causing proteins with cytosolic malate dehydrogenase.

In one embodiment, the present invention provides a method of treating a neurodegenerative disorder in a subject in need thereof, the method comprising administering to the subject a therapeutically effective amount of an agent capable of reducing an interaction between malate dehydrogenase and a conformationally altered or mutant protein, thereby treating a neurodegenerative disorder caused by complex formation of cytosolic malate dehydrogenase with a conformationally altered or mutant-causing protein. In another embodiment, the neurodegenerative disorder is amyotrophic lateral sclerosis (ALS). In another embodiment, the conformationally altered or mutant protein is a mutant SOD1 protein. In another embodiment, the mutant SOD1 protein is associated with ALS. In another embodiment, the agent is a peptide. In another embodiment, the agent is any peptide of the present invention. Each possibility represents a separate embodiment of the present invention.

In another embodiment, the present invention provides a method of treating a neurodegenerative disorder, the method comprising administering to an individual in need thereof a therapeutically effective amount of an agent capable of increasing brain mitochondrial respiration, thereby treating the neurodegenerative disorder, with the proviso that said agent is not pyruate or oxaloacetate. In another embodiment, the agent is capable of increasing cytoplasmic malate levels in a subject in need thereof. In another embodiment, the agent is a peptide agent. In another embodiment, the peptide agent comprises at least 4 amino acids of human malate dehydrogenase. In another embodiment, the agent comprises the sequence set forth in SEQ ID NO: 1. In another embodiment, the agent is any peptide of the present invention. Each possibility represents a separate embodiment of the present invention.

The agent of methods and compositions of the present invention is, in another embodiment, a peptide. In another embodiment, the peptide comprises a fragment of a malate dehydrogenase protein. In another embodiment, the malate dehydrogenase is a human malate dehydrogenase. In another embodiment, the malate dehydrogenase is any other malate dehydrogenase known in the art. Each possibility represents a separate embodiment of the present invention.

The ALS or neurodegenerative disorder treated by methods and compositions of the present invention is, in another embodiment, associated with a mutation in the gene encoding the human copper-zinc superoxide dismutase (hSOD1) protein. In another embodiment, the ALS or neurodegenerative disorder is caused by a mutation in the hSOD gene. In another embodiment, the hSOD mutation is a gain-of-function mutation. In another embodiment, the hSOD mutation is a toxic gain-of-function mutation. In another embodiment, the ALS or neurodegenerative disorder is of unknown etiology. Each possibility represents a separate embodiment of the present invention.

In another embodiment, the fragment of malate dehydrogenase is 4 amino acids in length. In another embodiment, the fragment is at least 3 amino acids in length. In another embodiment, the fragment is at least 5 amino acids in length. In another embodiment, the fragment is at least 6 amino acids in length. In another embodiment, the fragment is at least 7 amino acids in length. In another embodiment, the fragment is at least 8 amino acids in length. In another embodiment, the fragment is at least 9 amino acids in length. In another embodiment, the fragment is at least 10 amino acids in length.

In another embodiment, the fragment is at least 15 amino acids in length. In another embodiment, the fragment is at least 20 amino acids in length. In another embodiment, the fragment is at least 30 amino acids in length. In another embodiment, the fragment is at least 40 amino acids in length. Each possibility represents a separate embodiment of the present invention.

In another embodiment, the peptide comprises at least 4 consecutive amino acids of a malate dehydrogenase protein. In another embodiment, the peptide comprises at least 3 consecutive amino acids of a malate dehydrogenase protein. In another embodiment, the peptide comprises at least 5 consecutive amino acids of a malate dehydrogenase protein. In another embodiment, the peptide comprises at least 6 consecutive amino acids of a malate dehydrogenase protein. In another embodiment, the peptide comprises at least 7 consecutive amino acids of a malate dehydrogenase protein. In another embodiment, the peptide comprises at least 8 consecutive amino acids of a malate dehydrogenase protein. In another embodiment, the peptide comprises at least 9 consecutive amino acids of a malate dehydrogenase protein. In another embodiment, the peptide comprises at least 10 consecutive amino acids of a malate dehydrogenase protein. In another embodiment, the peptide comprises at least 15 consecutive amino acids of a malate dehydrogenase protein. In another embodiment, the peptide comprises at least 20 consecutive amino acids of a malate dehydrogenase protein. In another embodiment, the peptide comprises at least 30 consecutive amino acids of a malate dehydrogenase protein. In another embodiment, the peptide comprises at least 40 consecutive amino acids of a malate dehydrogenase protein. Each possibility represents a separate embodiment of the present invention.

A non-limiting example of a mutant SOD1 protein associated with ALS is G93A-hSOD1. In another embodiment, the mutant SOD1 protein is any other mutant SOD1 protein associated with ALS known in the art. As described herein, the present invention provides methods readily generalizable by one skilled in the art to treatment of a neurodegenerative disorder such as ALS caused by any mutant SOD1 protein, particularly a mutant SOD1 that associates with MDH. The mutant SOD1 protein causing the disease need not be the same as that used in testing the agent. Since many mutant SOD1 proteins will interact with MDH in substantially the same manner, the same agents can be used for different mutant SOD1 proteins. Each possibility represents a separate embodiment of the present invention.

In another embodiment, the peptide comprises the dimerization site of MDH1 with an SOD1 protein. In another embodiment, the peptide overlaps the dimerization site of MDH1 with an SOD1 protein. In another embodiment, the peptide falls within the dimerization site of MDH1 with an SOD1 protein. In another embodiment, the SOD1 protein is a mutant SOD1 protein. In another embodiment, the mutant SOD1 protein is associated with ALS. As a non-limiting example, the dimerization site of MDH1 with G93A-hSOD1 is depicted herein in FIG. 8. Each possibility represents a separate embodiment of the present invention.

In another embodiment, the peptide comprises the dimerization site of MDH1 with another neurodegenerative disease-causing protein. In another embodiment, the peptide overlaps the dimerization site of MDH1 with a neurodegenerative disease-causing protein. In another embodiment, the peptide falls within the dimerization site of MDH1 with another neurodegenerative disease-causing protein. In another embodiment, the other neurodegenerative disease causing protein is a conformationally altered or mutant protein. In another embodiment, the conformationally altered or mutant protein is associated with a neurodegenerative disorder. Each possibility represents a separate embodiment of the present invention.

In another embodiment, the present invention provides a fragment of MDH of 19-50 amino acids in length, the peptide comprising the sequence set forth in SEQ ID NO: 1. In another embodiment, the MDH fragment is 19-45 amino acids in length. In another embodiment, the MDH fragment is 19-40 amino acids in length. In another embodiment, the MDH fragment is 19-35 amino acids in length. In another embodiment, the MDH fragment is 19-30 amino acids in length. In another embodiment, the MDH fragment is 19-25 amino acids in length. In another embodiment, the MDH fragment is 25-45 amino acids in length. In another embodiment, the MDH fragment is 25-40 amino acids in length. In another embodiment, the MDH fragment is 25-35 amino acids in length. In another embodiment, the MDH fragment is 25-30 amino acids in length. In another embodiment, an MDH-derived peptide of the present invention is derived from wt MDH. In another embodiment, the peptide is derived from a mutant MDH. Each possibility represents a separate embodiment of the present invention.

Another non-limiting example of a peptide that disrupts a MDH1-G93A-hSOD1 complex is a peptide with a sequence set forth in SEQ ID NO: 1. In another embodiment, a peptide of methods and compositions of the present invention comprises the sequence set forth in SEQ ID NO: 1. In another embodiment, a peptide of methods and compositions of the present invention has the sequence set forth in SEQ ID NO: 1. In another embodiment, the peptide overlaps the sequence set forth in SEQ ID NO: 1. In another embodiment, the overlap is at least 10 amino acids in length. In another embodiment, the overlap is at least 8 amino acids in length. In another embodiment, the overlap is at least 6 amino acids in length. In another embodiment, the overlap is at least 12 amino acids in length. In another embodiment, the overlap is at least 14 amino acids in length. In another embodiment, the overlap is at least 16 amino acids in length. In another embodiment, the overlap is at least 18 amino acids in length. Each possibility represents a separate embodiment of the present invention.

In another embodiment, the present invention provides a pharmaceutical composition comprising a pharmaceutically acceptable carrier and, as an active ingredient, an agent capable of preventing an interaction between malate dehydrogenase and a conformationally altered or mutant protein, wherein the conformationally altered or mutant protein is associated with a neurodegenerative disorder. In another embodiment, the neurodegenerative disorder is amyotrophic lateral sclerosis (ALS). In another embodiment, the conformationally altered or mutant protein is an SOD1 protein. In another embodiment, the agent is a peptide agent. Each possibility represents a separate embodiment of the present invention.

In another embodiment, the agent of methods and compositions of the present invention is a small molecule. In another embodiment, the small molecule is selected from the group consisting of malate, octanoate, α-ketoglutarate, succinate and fumarate. In another embodiment, the small molecule is any other small molecule known in the art that is capable of up-regulating an activity of malate dehydrogenase. In another embodiment, the malate dehydrogenase is a cytosolic malate dehydrogenase. In another embodiment, the small molecule is any other small molecule known in the art that is capable of up-regulating acetyl coenzyme A. Each possibility represents a separate embodiment of the present invention.

In another embodiment of methods and compositions of the present invention, the conformationally altered or mutant protein is associated with Parkinson's Disease. In another embodiment, the protein is Alpha-synuclein. In another embodiment, the protein is Parkin. In another embodiment, the protein is PINK1. In another embodiment, the protein is DJ-1. In another embodiment, the protein is ATP13A2. In another embodiment, the protein is another protein for which mutations have been linked to Parkinson's disease. Each possibility represents a separate embodiment of the present invention.

In another embodiment, the conformationally altered or mutant protein is associated with Alzheimer's disease. In another embodiment, the protein is amyloid beta peptide (ABETA). In another embodiment, the protein is another protein for which mutations have been linked to Alzheimer's disease. Each possibility represents a separate embodiment of the present invention.

In another embodiment, the conformationally altered or mutant protein is a protein known to contain poly-glutamine repeats. In another embodiment, the protein is Huntingtin, for which mutations of its gene are known to be associated with Huntington disease. In another embodiment, the protein is androgen receptor, for which mutations of its gene are known to be associated with Kennedy disease (also known as spinal and bulbar muscular atrophy). Each possibility represents a separate embodiment of the present invention.

In another embodiment, the conformationally altered or mutant protein is microtubule-associated protein tau. Mutations of the gene encoding tau have been linked to Alzheimer's and other neurodegenerative diseases, such as Pick's disease (PID), progressive supranuclear palsy (PSP), corticobasal degeneration (CBD), and frontotemporal dementia and parkinsonism linked to chromosome 17 (FTDP-17).

In another embodiment, the present invention provides a method of identifying an agent capable of treating amyotrophic lateral sclerosis (ALS), the method comprising the steps of (a) contacting said agent with a known initial amount of a complex of a malate dehydrogenase protein and a mutant SOD1 protein, wherein said mutant SOD1 protein is associated with ALS; and measuring an amount of said complex in the presence of said agent, whereby, if said amount of said complex in the presence of said agent is less than said known initial amount, then said agent is capable of treating amyotrophic lateral sclerosis.

In another embodiment, the present invention provides a method of identifying an agent capable of treating ALS, the method comprising the steps of: (a) contacting a malate dehydrogenase protein with a mutant SOD1 protein, wherein the mutant SOD1 protein is associated with ALS, in the presence of the agent; (b) measuring the amount of complex formation between the malate dehydrogenase protein and the mutant SOD1 protein, following step (a); (c) contacting the malate dehydrogenase protein with the mutant SOD1 protein in the absence of the agent; and (d) measuring the amount of complex formation between the malate dehydrogenase protein and the mutant SOD1 protein, following step (c), whereby, if the amount of step (b) is less than the amount of step (d), then the agent is capable of treating amyotrophic lateral sclerosis.

In another embodiment, the present invention provides a method of identifying an agent capable of treating Parkinson's disease, the method comprising the steps of: (a) contacting a malate dehydrogenase protein with a mutant protein associated with Parkinson's disease, in the presence of the agent; (b) measuring the amount of complex formation between the malate dehydrogenase protein and the mutant protein, following step (a); (c) contacting the malate dehydrogenase protein with the mutant protein in the absence of the agent; and (d) measuring the amount of complex formation between the malate dehydrogenase protein and the mutant protein, following step (c), whereby, if the amount of step (b) is less than the amount of step (d), then the agent is capable of treating Parkinson's disease. In another embodiment, the mutant protein is Alpha-synuclein. In another embodiment, the mutant protein is Parkin. In another embodiment, the mutant protein is PINK1. In another embodiment, the mutant protein is DJ-1. In another embodiment, the mutant protein is ATP13A2. In another embodiment, the mutant protein is any other mutant protein known to be associated with Parkinson's disease. Each possibility represents a separate embodiment of the present invention.

In another embodiment, the present invention provides a method of identifying an agent capable of treating Alzheimer's disease, the method comprising the steps of: (a) contacting a malate dehydrogenase protein with a mutant protein associated with Alzheimer's disease, in the presence of the agent; (b) measuring the amount of complex formation between the malate dehydrogenase protein and the mutant protein, following step (a); (c) contacting the malate dehydrogenase protein with the mutant protein in the absence of the agent; and (d) measuring the amount of complex formation between the malate dehydrogenase protein and the mutant protein, following step (c), whereby, if the amount of step (b) is less than the amount of step (d), then the agent is capable of treating Alzheimer's disease. In another embodiment, the mutant protein is amyloid beta peptide (ABETA). In another embodiment, the mutant protein is any other mutant protein known to be associated with Alzheimer's disease. Each possibility represents a separate embodiment of the present invention.

In another embodiment, the present invention provides a method of identifying an agent capable of treating Huntington disease, the method comprising the steps of: (a) contacting a malate dehydrogenase protein with a mutant protein associated with Huntington disease, in the presence of the agent; (b) measuring the amount of complex formation between the malate dehydrogenase protein and the mutant protein, following step (a); (c) contacting the malate dehydrogenase protein with the mutant protein in the absence of the agent; and (d) measuring the amount of complex formation between the malate dehydrogenase protein and the mutant protein, following step (c), whereby, if the amount of step (b) is less than the amount of step (d), then the agent is capable of treating Huntington disease. In another embodiment, the mutant protein is Huntingtin. In another embodiment, the mutant protein is another protein known to contain poly-glutamine repeats. In another embodiment, the mutant protein is any other mutant protein known to be associated with Huntington disease. Each possibility represents a separate embodiment of the present invention.

In another embodiment, the present invention provides a method of identifying an agent capable of treating Kennedy disease (also known as spinal and bulbar muscular atrophy, the method comprising the steps of: (a) contacting a malate dehydrogenase protein with a mutant protein, wherein the mutant protein is associated with Kennedy disease, in the presence of the agent; (b) measuring the amount of complex formation between the malate dehydrogenase protein and the mutant protein, following step (a); (c) contacting the malate dehydrogenase protein with the mutant protein in the absence of the agent; and (d) measuring the amount of complex formation between the malate dehydrogenase protein and the mutant protein, following step (c), whereby, if the amount of step (b) is less than the amount of step (d), then the agent is capable of treating Kennedy disease. In another embodiment, the mutant protein is androgen receptor. In another embodiment, the mutant protein is another protein known to contain poly-glutamine repeats. In another embodiment, the mutant protein is any other mutant protein known to be associated with Kennedy disease. Each possibility represents a separate embodiment of the present invention.

In another embodiment, the present invention provides a method of identifying an agent capable of treating a neurodegenerative disorder, the method comprising the steps of: (a) contacting a malate dehydrogenase protein with a mutant microtubule-associated protein tau, wherein the mutant tau protein is associated with the neurodegenerative disorder, in the presence of the agent; (b) measuring the amount of complex formation between the malate dehydrogenase protein and the mutant tau protein, following step (a); (c) contacting the malate dehydrogenase protein with the mutant tau protein in the absence of the agent; and (d) measuring the amount of complex formation between the malate dehydrogenase protein and the mutant tau protein, following step (c), whereby, if the amount of step (b) is less than the amount of step (d), then the agent is capable of treating the neurodegenerative disorder. In another embodiment, the neurodegenerative disorder is Alzheimer's disease. In another embodiment, the neurodegenerative disorder is Pick's disease (PID). In another embodiment, the neurodegenerative disorder is progressive supranuclear palsy (PSP). In another embodiment, the neurodegenerative disorder is corticobasal degeneration (CBD). In another embodiment, the neurodegenerative disorder is frontotemporal dementia with parkinsonism linked to chromosome 17 (FTDP-17). In another embodiment, the neurodegenerative disorder is any other neurodegenerative disorder linked to a mutant tau protein. Each possibility represents a separate embodiment of the present invention.

In another embodiment, a complex of the present invention is fluorescently labeled. In another embodiment, the step of measuring an amount of a malate dehydrogenase-mutant SOD1 complex is performed by measuring a signal from the complex. In another embodiment, the signal is fluorescence signal. In another embodiment, the signal is a FRET signal. In another embodiment, an alteration in the signal is measured following addition of the test agent. In another embodiment, the signal is generated using FRET. In another embodiment, the signal is any other type of signal known in the art that can be engineered to be dependent on an intact malate dehydrogenase-mutant SOD1 complex. As described herein, the present invention provides methods readily generalizable by one skilled in the art to any type of quantitative or semi-quantitative signal that can be engineered to be dependent on an intact malate dehydrogenase-mutant SOD1 complex. Each possibility represents a separate embodiment of the present invention.

Embodiments of the present invention provide agents and method of using same for treating neurodegenerative disorders, such as ALS. In some embodiments the agents are peptide agents such as peptides or small molecules which can interfere with binding of cytoplasmic malate dehydrogenase to ALS-related SOD1 or abrogating the inhibition of the malate-aspartate shuttle in the neurons. Additional embodiments of the present invention provide novel methods of screening for agents capable of interfering with binding of cytoplasmic malate dehydrogenase to SOD1.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein below.

Peptide bonds (—CO—NH—) within the peptide may be substituted, for example, by N-methylated bonds (—N($CH_3$)—CO—), ester bonds (—C(R)H—C—O—O—C(R)—N—), ketomethylene bonds (—CO—$CH_2$—), α-aza bonds (—NH—N(R)—CO—), wherein R is any alkyl, e.g., methyl, carba bonds (—CH2-NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted by synthetic non-natural acid such as TIC, naphthylalanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Ile | I |
| leucine | Leu | L |
| Lysine | Lys | K |
| Methionine | Met | M |
| Phenylalanine | Phe | F |
| Proline | Pro | P |

TABLE 1-continued

| Amino Acid | Three-Letter Abbreviation | One-letter Symbol |
|---|---|---|
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |

TABLE 2-continued

| Non-conventional amino acid | Code | Non-conventional amino acid | Code |
|---|---|---|---|
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclo-hexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclo-hexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |

TABLE 2-continued

| Non-conventional amino acid | Code | Non-conventional amino acid | Code |
|---|---|---|---|
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α ethylvaline | Mtrp | L-α-methyltyrosine | Mtyr |
| L-α-methylleucine | Mval | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino) cyclopropane | Nmbc | | |

The peptides of the present invention are preferably utilized in a linear form, although it will be appreciated that in cases where cyclization does not severely interfere with peptide characteristics, cyclic forms of the peptide can also be utilized.

The peptides of the present invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. Further description of peptide synthesis is disclosed in U.S. Pat. No. 6,472,505.

A preferred method of preparing the peptide compounds of the present invention involves solid phase peptide synthesis.

Large scale peptide synthesis is described by Andersson Biopolymers 2000; 55(3):227-50.

The peptides of the present invention may be delivered to the subject using gene therapy techniques or as peptide molecules.

It will be appreciated that since the agents of the present invention are peptides they are susceptible to break-down by the enzymes in the stomach. In order to improve drug delivery therefore, the peptide agents of the present invention may be combined with a mucoadhesive agent. Various mucoadhesive agents, e.g., mucoadhesive polymers are known which are believed to bind to the mucus layers coating the stomach and other regions of the gastrointestinal tract. Examples of mucoadhesive polymers as discussed herein include, but are not limited to chitosan, polyacrylic acid, hydroxypropyl methylcellulose and hyaluronic acid. Most preferably, the mucoadhesive polymer is chitosan [Guggi et al., (2003) J of Controlled Release 92:125-135].

It will further be appreciated that delivery of peptide agents to the brain is restricted by the blood brain barrier. Over the years, several strategies to circumvent the blood brain barrier have been proposed, such as by transient osmotic opening of the BBB, high dosing (e.g., of chemotherapy), use of carrier systems such as antibodies, or even biodegradable implants. All these systems are contemplated by the present invention.

Furthermore, several synthetic NP polymers, arranged as spheres have been studied as carriers of drugs across the BBB. Poly(butyl cyanoacrylate) has been reported to effectively deliver different drugs, including peptides [Kreuter J. Adv. Drug Delivery Rev. 2001, 47:65-81; Gulayev A E, et al., Pharm Res 1999, 16:1564-9].

It has also been suggested that liposomes can enhance drug delivery to the brain across the blood-brain barrier [Umezawa and Eto, Biochem. Biophys. Res. Comm. 153:1038-1044 (1988); Chan et al., Ann. Neurol, 21:540-547 (1987); Laham et al., Life Sciences 40:2011-2016 (1987); and Yagi et al., J. APRlo Biocheme 4:121-125 (1982)]. Liposomes are small vesicles (usually submicron sized) comprised of one or more concentric bilayers of phospholipids separated by aqueous compartments.

It has been suggested that the use of an external ligand such as mannose can improve a liposomal particle's ability to cross the BBB [Huitinga et al., J exp Med 172 (1990) 1025-33; Umezawa F., Biochem Biophys Res Commun 153 (1988) 1038-44]. The mannosylated liposomes were shown to be incorporated in glial cells as opposed to neuronal cells, the former having a receptor for mannose [Umezawa F., Biochem Biophys Res Commun 153, 1988, 1038-44]. PCT Application, Publication No. WO9402178A1 to Micklus discusses the coupling of liposomes to an antibody binding fragment which binds to a receptor molecule present on the vascular endothelial cells of the mammalian blood-brain barrier. The peptides perhaps may also be delivered by phages, or in a liquid or solid formulation, intranasally for example.

The peptides or small molecules of the present invention may be used to treat neurodegenerative disorders. Examples of neurodegenerative disorders include, but are not limited to Amyotrophic lateral sclerosis (ALS), Alzheimer's Dementia, Alexander disease, Alper's disease, Ataxia telangiectasia, Batten disease, Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson disease, Pelizaeus-Merzbacher Disease, Pick's disease, Primary lateral sclerosis, Prion diseases, Refsum's disease, Sandhoff disease, Schilder's disease, Schizophrenia, Spielmeyer-Vogt-Sjogren-Batten disease, Spinocerebellar ataxia and Spinal muscular atrophy.

The peptides or small molecule agents of the present invention may be delivered to the subject per se or as part of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the DJ-1 peptides of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient i.e. the brain.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., neurodegenerative disorder) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Experimental Details Section

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXAMPLES

Materials

Dulbecco's modification of Earle's medium (DMEM), heat-inactivated fetal calf serum (FCS), L-glutamine, penicillin streptomycin and EZ-First Strand cDNA Synthesis RNA kit, L-glutamine, G418 and antibiotics were obtained from Biological Industries (Beit Haemek, Israel); Doxycyclin, thiazol blue (MTT), alcohol dehydrogenase, PES, Hygromycin B NADH and NAD from Sigma (Sigma-Aldrich, St. Louis, Mo.); Lipofectamin 2000 from Invitrogen (San Diego, Calif.); (rabbit) anti-human SOD1 antibodies from Santa Cruz, Inc. (USA); polyclonal (rabbit) anti-GFP, from Abcam (UK); goat anti rabbit-IRDey-800 from Li-Cor; Taq DNA polymerase from Bioline (Luckenwalde, Germany); SMART cDNA synthesis kit pEGFP pECFP, pEYFP and pTRE2hyg plasmids from Clonetech; malic and lactic acid determination kits from ENZYTEC (Germany); µ-slide 8 well plates from Ibidi (Germany); protein A-sepharose from Amersham Bioscience; Ampicillin from Applichem; and pQBI25 fc1,2,3from (Qbiogene/MP Biomedicals [Irvine, Calif.]).

Stable Cell Lines Expressing Inducible Forms of G93A-hSOD1-GFP and WT-hSOD1-GFP

NSC-34 cells were provided by Dr. Neil Cashman. pcDNA3.1 plasmids containing wild-type or G93A-mutant hSOD1 cDNA were provided by Dr. David Gozal. NSC-34 cell lines stably expressing an inducible form of WT-hSOD1 or G93A-hSOD1 fused with GFP at the C-terminal end were obtained by cotransfection with pUHD 172-1 and pTRE2hyg-WT-hSOD1-GFP or pTRE2hyg-G93A-hSOD1-GFP cDNA.

Cell Culture

NSC-34 cells were grown in DMEM supplemented with 5% heat-inactivated FCS, 1 mM glutamine, and antibiotics (100 IU/mL penicillin and 100 µg/mL streptomycin) at 37° C. in a 5% $CO_2$ humidified atmosphere. WT-hSOD1 and G93A-hSOD1 cell lines were kept in selection by addition of G418 (700 µg/mL) plus hygromycin B (200 ug/mL) until used. Cells were incubated with doxycycline (1 µg/mL; 24 h) to induce expression of WT-hSOD1-GFP and G93A-hSOD1-GFP proteins.

Mouse Spinal Cord and Motor Cortex cDNA Library Construction.

Freshly excised brains and spinal cords of C57 black mice that were sacrificed for another research project were donated by Dr D M Michaelson. Total RNA was prepared from the freshly excised tissues using EZ-RNA preparation kit. Aliquots (1 ug) of total RNA were subjected to cDNA synthesis using the SMART cDNA synthesis kit according to user manual. The first strand was subjected to PCR amplification using a primer 5'-CCTAGCGGCCGCAAGCAGTGGTAT-CAACGCAGAGT-3' (SEQ ID NO: 3) that included a NotI restriction site. The cDNA was digested with NotI and subjected to ligation with a set of 3 vectors pQBI25 fc1,2,3 that contains the blue fluorescence protein (BFP) encoding sequence. Ligation products were electroporated into DH5α bacteria, to obtain 1*10^6 clones.

To assess library variability, a representative amount of colonies from the transformed DH5α, were subjected to PCR analysis using the following primers: Forward 5'-CATTAC-CTGTCCACACAATCTGCCC-3' (SEQ ID NO: 4) Reverse 5'-CACCTACTCAGACAATGCGATGC-3' (SEQ ID NO: 5). The library was amplified overnight in 2XTY media containing ampicillin. Bacterial pellets were collected by centrifugation and suspended in 5 ml of 2XTY+15% glycerol and frozen at −70° C. until use.

FRET Analysis

Construction of pQBI-BFP-GFP plasmid: A plasmid containing a BFP-GFP chimera was prepared in order to serve as a positive control for the FRET studies. pQBI25 plasmid was digested with ClaI and NotI. pEGFP plasmid was used to obtain GFP DNA by PCR amplification using the following primers: Forward 5'-CTCAGATATCGATCTCAAGCT-3' (SEQ ID NO: 6) Reverse 5'-CCTCTACAAATGTGGTATG-GCTG-3' (SEQ ID NO: 7). The GFP DNA was digested with ClaI and NotI and subjected to ligation with the pQBI25 plasmid with a 23 amino acid linker.

FRET Live Cell Screening: The mouse cDNA library, the pQBI-BFP-GFP and pQBI plasmids were transfected into the WT-hSOD1-GFP and G93A-hSOD1-GFP cells using lipofectamine transfection reagent. After 24 h, 1 ug/ml doxycycline was added to induce expression of the hSOD1-GFP chimera. 24 h later, cells were washed with PBS harvested and analyzed by fluorescence activated cell sorting (FACS) using an excitation UV laser set at 0.133 W and a 530/30 nm emission filter.

pQBI-BFP-GFP transfected NSC-34 cells and pQBI-BFP-GFP transfected WT-hSOD1-GFP and G93A-hSOD1-GFP cells were used to identify cells with positive FRET signal. pQBI25 (which contains the BFP) transfected WT-hSOD1-GFP and G93A-hSOD1-GFP were used to evaluate FRET signals coming from interactions between the BFP and GFP moieties. The gating area was set on the population defined by a positive FRET signal. The WT-hSOD1-GFP and G93A hSOD1-GFP cells transfected with the mouse spinal cord and motor cortex library were subjected to FACS to sort out cells showing a positive FRET signal.

Total RNA was extracted from each of the sorted cells and subjected to RT using EZ-First Strand cDNA Synthesis RNA kit followed by PCR amplification with the following primers: Forward 5'-CATTACCTGTCCACACAATCTGCCC-3' (SEQ ID NO: 8) Reverse 5'-CACCTACTCAGACAATGC-GATGC-3' (SEQ ID NO: 9). PCR products were digested with NotI and recloned into pQBI50fc1,2,3 plasmids. Of these clones 60 individual clones were sequenced. The clones that appeared repeatedly in the G93A-hSOD1 but not WT-hSOD1 were selected for further confocal FRET and co-immunoprecipitation studies.

Confocal FRET Analysis

YFP CFP fluorophores plasmids: The pECFP plasmid containing the CFP (cyan fluorescence protein) was digested with AgeI and HindIII and subjected to ligation with the pcDNA3.1 plasmids containing WT-hSOD1 and G93A-hSOD1 cDNA. A set of 3 vectors pEYFP fc1,2,3 containing NotI restriction site were prepared. Thus, pEYFP was digested with EcoRI and BamHI and subjected to ligation with 3 pairs of frame-shifted oligonucleotides, each containing NotI and EcoRV sites with the following sequences:

```
Frame 1 Sense
                                       (SEQ ID NO: 10)
5'-AATTCTGCGATATCGCGGCCGCG-3';

Anti sense
                                       (SEQ ID NO: 11)
5'-GATCCGCGGCCGCGATATCGCA-3';

Frame 2 sense
                                       (SEQ ID NO: 12)
5'-AATTCTGCCGATATCGCGGCCGCG-3';

anti sense
                                       (SEQ ID NO: 13)
5'-GATCCGCGGCCGCGATATCGGCA-3';

Frame 3 sense
                                       (SEQ ID NO: 14)
5'-AATTCTGCCCGATACGCGGCCGCG-3';

anti sense
                                       (SEQ ID NO: 15)
5'-GATCCGCGGCCGCGATATCGGGCA-3'.
```

Selected clones from the FACS sorted FRET positive clones were cloned into the suitable pEYFP vector to yield a pEYFP-derivative of the selected clones and subjected to confocal FRET analysis.

Confocal FRET analysis: 1*10^5 NSC-34 cells/well were plated in a p-slide 8 wells slide. Cells were transfected with pECFP-G93A-hSOD1 and pECFP-WT-hSOD1 with and without pEYFP-derivative of the selected clones. In addition, cells were transfected with pEYFP-derivative of the selected clones or the control pEYFP alone. Transfected cells were grown for 48 h and subjected to ZEISS confocal microscopy. Emission spectra of CFP and YFP were collected using laser excitation of 405 and 514 nm respectively, and an emission window of 10 nm between 449 to 599 for the CFP excitation and an emission window of 10 nm between 524 to 599 for the YFP excitation. The FRET efficiency was calculated as described (14). One clone expressing cytosolic malate dehydrogenase (cytMDH) showed a high FRET efficiency and was chosen for further co-immunoprecipitation studies.

Pull-Down Immunoprecipitation

NSC-34 cells were cotransfected with pCDNA3.1-WT-hSOD1 and pEYFP-cytMDH or with pCDNA3.1-G93A-hSOD1 and pEYFP-cytMDH. After 48 hours cells were lysed in solubilization buffer (50 mM Hepes PH7.5, 150 mM NaCl, 10% glycerol, 1% Triton-X, 1 mM EDTA, 1 Mm EGTA and 1.5 mM $MgCl_2$). Samples containing 0.5 mg protein were subjected to immunoprecipitation using anti hSOD1 antibodies immobilized on protein A-coupled sepharose beads. The beads were washed and proteins were solubilized in SDS loading buffer. Samples were boiled for 3 min and subjected to SDS 7.5% polyacrylamide gel electrophoresis and immunoblotting.

Immunoblotting and Quantification of SOD1 Derivatives and YFP-Tagged MDH

Cells were solubilized in 50 mM Hepes buffer pH-7.5 containing 150 mM NaCl, 10% glycerol, 1% Triton X-100, 1 mM EDTA, 1 mM EGTA and 1.5 mM MgCl2). Cell lysates were diluted with sodium dodecyl sulfate (SDS) loading buffer. The mixture was boiled for 3 min and stored at $-80°$ C. for subsequent analysis. Proteins (100 µg per lane) were subjected to 7.5% (v/v) SDS-polyacrylamide gel electrophoresis and the resolved proteins were electroblotted onto nitrocellulose membranes. Nonspecific binding sites on the nitrocellulose membranes were blocked by incubation for 1 h with 5% (w/v) non-fat milk in Tris-buffered saline (TBST), containing 150 mM NaCl, 10 mM Tris-HCl, pH 7.4, and 0.1% (v/v) Tween-20. The nitrocellulose membranes were incubated overnight at 4° C. with primary antibodies (anti human SOD1; anti-GFP; anti-β-actin) diluted 1:1000 in TBST with 1% (w/v) bovine serum albumin. After washing in TBST, the nitrocellulose membranes were incubated for 1 h at room temperature (20° C.) with IRDey-800-linked secondary antibodies, diluted 1:10,000 in TBST, washed in TBST and subjected to analysis on the odyssey fluorescence reader from Li-Cor bioscience.

Preparation of Mitochondria and Cytosol Fractions $3.5*10^6$ G93A-hSOD1-GFP and WT-hSOD1-GFP cells were plated (12 plates of 10 cm each). Doxycycline (1 ug/ml) was added after 24 h to half of the plates and 48 h later cells scraped off the plates, cells from each two plates were combined, collected by centrifugation. Cells pellets were suspended in 500 ul of 10 mM Tris-HCl buffer pH-7.4 containing 250 mM sucrose, and 2 mM EDTA. Cells were subjected to 3 rounds of freezing/thawing. 0.5 gr of glass beads (60 mesh) were then added and tubes were vortexed 3 times and centrifuged (2000 rpm 5 min). The supernatants (containing the cytosol and mitochondria) were collected and centrifuged at 10,000 rpm for 15 min. Supernatants (cytosol) and pellets (mitochondria) were collected. The pellets were suspended in 250 ul of 10 mM Tris-HCl buffer pH-7.4 containing 250 mM sucrose, and 2 mM EDTA containing 0.5% Tween.

Assessment of MDH Enzymatic Activity

Aliquots of the cytosolic fractions were incubated with 100 mM potassium phosphate buffer pH 7.4 containing 2 mM NADH. Reaction started with the edition of 10 mM oxaloacetate and the decrease in NADH was measured on 'ultraspec 2000' at 340 nm for 3 min at 3 sec intervals.

Lactate and Malate Assays

Aliquots (100 ul) aliquots of the cytosol fractions were used for determinations of lactate and malate concentrations with Enzytec™ lactic and malic acids determination kits.

NADH $NAD^+$ Measurements $NAD^+$ and NADH concentrations were measured by spectrophotometric enzymatic cycling assay as described (15). For NADH determination 50 µl aliquots the cytosol and mitochondrial suspensions were diluted in 1N NaOH to yield 0.2N NaOH concentration and heated at 60° C. for 20 min to destroy $NAD^+$. For total NADH and $NAD^+$ determination 50 ul aliquots the cytosol and mitochondrial suspensions were diluted in 1N NaOH to yield 0.2N NaOH concentration without heating. 15 ul aliquots of the heated and non-heated samples were incubated with 200 ul cycling assay mix, containing 100 mM Tris-HCl, 2 mM PES 0.5 mM thiazol blue, 0.2 mg/ml alcohol dehydrogenase and 0.6M ethanol at 37° C. for 10 min. $NAD^+$ Absorption was read at OD 570 nm (Linear range 1-80 nM NADH or $NAD^+$).

Screening for Peptide Agents that Inhibit the Association of MDH1 with Disease Proteins The screening method was based on the fluorescence resonance energy transfer (FRET) system between cyan fluorescence protein (CFP) chimera proteins and yellow fluorescence protein (YFP) chimera proteins. The present inventors designed and used this system to identify the specific interaction of G93A SOD1 with MDH1 so as to identify a motif within MDH1 that is critical for the G93A SOD1-MDH1 interaction. The agents tested were peptides derived from MDH1.

A Myc-tagged peptide library expressing small fragments of the MDH1 was prepared. MDH1 cDNA was digested with AluI or/and DpnI and the fragments were cloned so that each peptide was placed in the correct reading frame of the original protein and in frame to the human myc tag sequence. G93A SOD1-CFP and MDH1-YFP expression plasmids were transfected into NSC-34 cells with and without the myc-tagged library.

The hypothesis is that the specific MDH1-derived peptides comprising the interacting motif will compete with MDH1 for the G93A SOD1-MDH1 interaction site. In such case, the CFP and YFP fluorescence of the G93A SOD1-CFP and MDH1-YFP will still be present, but the FRET signal will be diminished. The screening studies were performed using a cell sorter (FACS) with 405 nm excitation laser and a 530/30 nm emission filter. CFP tagged cells that showed no FRET signal were sorted out. RNA was extracted from the sorted cells, converted into cDNA and subjected to PCR amplification in order to amplify the peptides DNA sequences.

The DNA sequence from the sorted cells was re-cloned. Four clones were obtained, one corresponding to amino acids 14-27 of the cytMDH protein GQIAHSLLYSIGNG (SEQ ID NO: 2) and three corresponding to amino acids 217-239 of the cytMDH protein SWLKGEFITTVQQRGAAVIKARK (SEQ ID NO: 1). The identified clones were re-analyzed in the FACS-based system to verify their ability to compete for the G93A SOD1-MDH1 interaction at 1:1:1 ratio levels. Thus, $5*10^6$ NSC-34 cells were transfected with equal amounts of G93A-hSOD1-CFP and cytMDH-YFP and the suspected myc-tagged cytMDH peptide-expressing plasmids. Peptides that prevented the FRET, namely those that shifted the cell population toward the FRET negative gating area, were considered to impair the G93A-hSOD1-CFP/cytMDH-YFP interaction.

Only one of two clones prevented the FRET under these conditions. The identified myc-tagged peptide was sequenced and identified as amino acids 217-239 of the cytMDH protein SWLKGEFITTVQQRGAAVIKARK (SEQ ID NO: 1).

Functional Assays

The functional significance of the loss of such interaction was assessed by alleviation of the rotenone (a mitochondrial inhibitor) or low-glucose challenge in NSC-34 clones expressing an inducible form of the mutant G93A SOD1-GFP as monitored by cell survival. The SWLKGEFITTVQQRGAAVIKARK (SEQ ID NO: 1) peptide was synthesized (SBS Gentech Beijing) with 5,6-TAMRA modification (to allow detection) at the N-terminus. The TAMRA-modified peptide was dissolved in 10% acetic acid and added to cell culture medium in culture medium containing 1% ethanol. Thus, 15,000 cells (WT-hSOD1 or G93A-hSOD1) seeded in each well of a 96-well plate in DMEM, 10% serum. 24 hours later, cells were incubated with $1*10^-6M$ cytMDH peptide (or acetic acid/ethanol vehicle) for 4 h without serum. 1-10 micromole/L Rotenone in DMEM, 10% serum was then added for 24 hours, or medium replaced with low glucose (1 mg/ml) in DMEM with 5% serum for 72 hours. Cell survival was then assessed. It was expected that if the identified peptide interaction is resolving the gain of toxic interaction of G93A SOD1-GFP, then survival of the cells upon rotenone- or low-glucose challenge will improve.

Determination of Octanoic Acid Effect 15,000 cells (WT-hSOD1 or G93A-hSOD1) were seeded in each well of a 96 well-plate in DMEM, 10% serum. 24 hours later, the cells were incubated with 3 mM octanoic acid with and without 1-10 micromole/L rotenone in DMEM, 10% serum for 24 hours. Or, cells were incubated with 3 mM octanoic acid and medium replaced with regular (5 mg/L) or low (1 mg/ml) glucose in DMEM with 5% serum for 72 hours. Cell survival was then assessed. It was expected that if the gain of toxic interaction of G93A SOD1-GFP is due to inhibition of the malate-aspartate shuttle, octanoic acid will provide an alternative energy source through the alternative shunt and the survival of the cells upon rotenone or low-glucose challenge will improve.

Cell Survival

Cell survival was assessed by the methylene blue assay. Cells were fixed with 4% formaldehyde solution for 1 h, then washed with 0.1M sodium borate buffer pH8.5, stained with 1% methylene blue for 20 min and washed with water. Cell-bound dye was eluted with 200 µl of 0.1M HCl. The optical density was assessed at 595 nm in ELISA plate reader.

Results

EXAMPLE 1

FRET Analysis Reveals G93A-hSOD1 Interaction with cytMDH

For the initial screening, two motor neuron-derived cell lines (NSC-34) were used that were stably transfected with a gene that inducibly expresses the diseased (G93A) and WT hSOD1 genes fused with green fluorescent protein (GFP) at their C-terminal end, to be used as FRET acceptors. A cDNA chimera library was generated from mouse spinal and cortical motor neurons wherein the clones were fused with BFP at the N-terminal end, to be used as FRET donors. The screening studies were performed using a cell sorter (FACS) to collect cells showing positive FRET signals. In principle, emission of the acceptor (GFP) during donor (BFP) excitation should indicate a positive FRET signal and thus be interpreted as evidence of proximity of the donor- and acceptor-tagged proteins. However, because of overlap in GFP and BFP spectra, the measured GFP emission caused by FRET is always contaminated by both direct excitation of GFP and by BFP emission in the GFP range. To overcome these problems, a BFP-GFP chimera was first constructed to serve as a positive control for the FRET signal and set the FACS gating area on the population defined by a positive FRET signal. FIG. 1 depicts FACS analysis of the BFP-GFP chimera and BFP expression plasmids transfected into the G93A-hSOD1-GFP (FIG. 1A) and the parent NSC-34 (FIG. 1B) cell line. FACS analysis of the G93A-hSOD1-GFP cells transfected with the GFP-BFP chimera reveals two distinct cell populations (R1 and R2). Only one of these populations (R2) is present in the parent NSC-34 cells transfected with the BFP-GFP chimera in the absence of the GFP-tagged hSOD1, thus identifying R1 as contaminating (non-FRET) fluorescence from the GFP-tagged h-SOD1 protein. FACS analysis of the G93A-hSOD1-GFP cells transfected with BFP (FIG. 1C) revealed a single population of cells (R1) that corresponded to the non-FRET fluorescence of the GFP fluorophore and no contaminating BFP emission. R2 was thus defined as a positive FRET population. This FRET-positive cell population is thus only generated when proteins from the BFP-tagged library are in close proximity with G93A-hSOD1-GFP or WT-hSOD1-GFP. The FACS gating area was thus set on the R2 population to sort out cells in which there is an apparent association between the hSOD1-GFP derivatives and a BFP-tagged candidate protein from the mouse motor-cortex spinal cord library.

G93A-hSOD1-GFP and WT-hSOD1-GFP NSC-34 cells were transfected with the BFP-tagged library and induced to express the hSOD1 proteins. Single cells demonstrating a positive FRET signal were sorted out using FACS. The initial screening identified a number of FRET positive, candidate BFP-tagged proteins that appeared to differentially interact with G93A-hSOD1-GFP but not WT-hSOD1-GFP. The most frequently occurring ones were HSP-70, which has already been shown to interact with hSOD1 (16), myelin, aldolase-1a, transferrin, the 3' end of kinesin-5a and cytosolic malate dehydrogenase (cytMDH).

EXAMPLE 2

Confirmation of G93A-hSOD1-cytMDH Interaction by Confocal Microscopy Using a Different Fluorophore Pair The interaction between each of the candidate proteins and the G93A-hSOD1 and WT-hSOD1 proteins was further characterized at the single-cell level by confocal microscopy, this time using a different set of donor (CFP) and acceptor (YFP) fluorophores to exclude the possibility of identifying protein interactions driven by the fluorophores themselves. Expression plasmids encoding G93A-hSOD1 and WT-hSOD1 fused to CFP were prepared as FRET donors, and plasmids encoding YFP fused with each of the candidate interacting proteins were prepared as FRET acceptors. CFP was attached to the C-terminus of SOD1, and YFP was attached to the N-terminal of the candidate protein. NSC-34 cells were transfected transiently with either G93A-hSOD1 or WT-hSOD1 fused to CFP expression plasmids and/or expression plasmids encoding YFP fused to candidate interacting proteins, and the interaction was assessed 48 hours later by FRET confocal microscopy. FRET was measured as enhanced emission of the acceptor (YFP) during donor (CFP) excitation. However, because of overlap in CFP and YFP spectra, measured YFP emission caused by FRET is contaminated by both direct excitation of YFP and by CFP emission in the YFP range. To overcome these limitations, FRET efficiency was quantified using spectrum measurements as described (14). Emission spectra were obtained upon excitation of the donor at 405 nm of cells expressing G93A-hSOD1-CFP and YFP-tagged candidate protein (FIG. 2A, data set A). The FRET-related YFP emission (F405) was extracted by subtracting the CFP spectrum collected from control cells expressing the G93A-hSOD1-CFP alone (FIG. 2A, data set B). The YFP spectrum upon direct excitation of the acceptor (F514) was also measured. The (F405/F514) ratio of the emission spectra obtained upon excitation at 405 nm and 514 nm of cells expressing G93A-hSOD1-CFP and YFP-tagged candidate protein was calculated (RatioA; FIG. 2B). Similarly the ratio (F405/F514) of the emission spectra obtained upon excitation at 405 nm and 514 nm of cells expressing only the YFP-tagged protein was calculated (RatioA0; FIG. 2B). Because RatioA is not dependent on wavelength, it was used to check for significant contaminations by other fluorescence sources (14). The difference (RatioA−RatioA0), that is directly proportional to FRET efficiency, was evaluated as an indicator of proximity. Similar measurements were performed for cells expressing WT-hSOD1-CFP and YFP-tagged candidate protein (FIG. 2C, data set A) and WT-hSOD1-CFP alone (FIG. 2C, data set B). RatioA and RatioA0 were assessed accordingly (FIG. 2D). Of the six candidate proteins identified in the screening only YFP-cytMDH demonstrated a positive FRET signal in this system with G93A-hSOD1-CFP (FIGS. 2A-B). No such signal was seen with WT-hSOD1-CFP (FIGS. 2C-D). Thus, as demonstrated in FIG. 2, only the G93A SOD1 cytMDH-expressing cells exhibited emission within the acceptor emission wavelength after excitation with the donor excitation wavelength.

EXAMPLE 3

Confirmation of G93A-hSOD1-cytMDH Interaction Using Co-Immunoprecipitation

Figure 3:
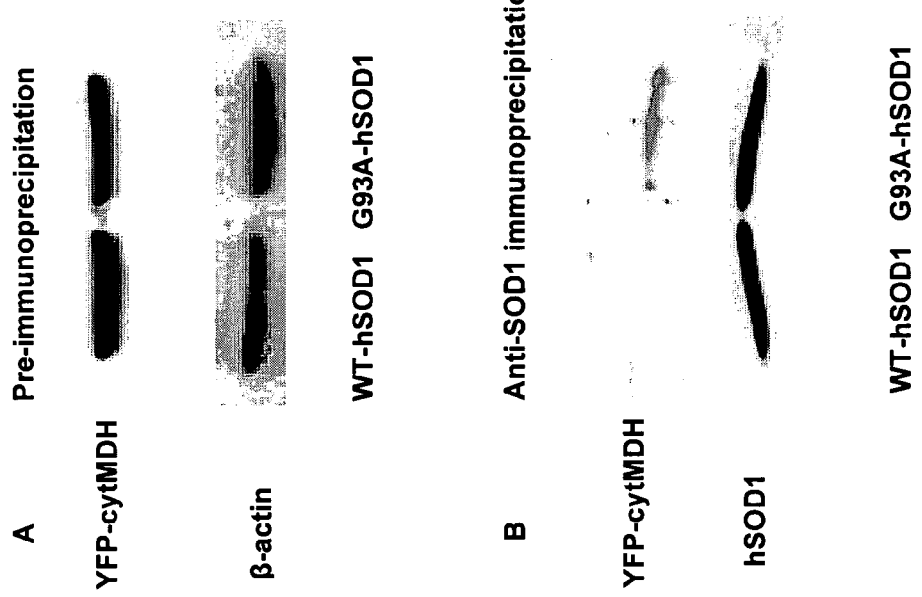
FIG. 3. Co-immunoprecipitation of cytMDH with hSOD1. NSC-34 cells were co-transfected with YFP-cytMDH and untagged WT-hSOD1 or untagged G93A-hSOD1 solubilized 48 h later and subjected to immunoprecipitation with anti-hSOD1 antibodies. A) Western blot of YFP-cytMDH and actin in samples pre-immunoprecipitation. B) Western blot of YFP-cytMDH and hSOD1 derivatives in the immunoprecipitated proteins.

Co-immunoprecipitation studies were next performed to further confirm the G93A-hSOD1 cytMDH interaction. To avoid complex formation due to excess of one of the potentially interacting proteins, parent NSC-34 cells were co-transfected with equal amounts of untagged WT-hSOD1 or G93A-hSOD1 and cytMDH-YFP. Cells were lysed, and immunoprecipitation was performed with anti-hSOD1 antibody. The precipitated proteins were subjected to SDS gel electrophoresis followed by immunoblotting with anti GFP antibody. As depicted in FIG. 3, comparable amounts of CFP-tagged G93A-hSOD1 and WT-hSOD1 vs. cytMDH-YFP were expressed. cytMDH-YFP was co-immunoprecipitated with G93A-hSOD1 but not with WT-hSOD1, thus further confirming the cytMDH-YFP-G93A-hSOD1 interaction.

Figure 4:
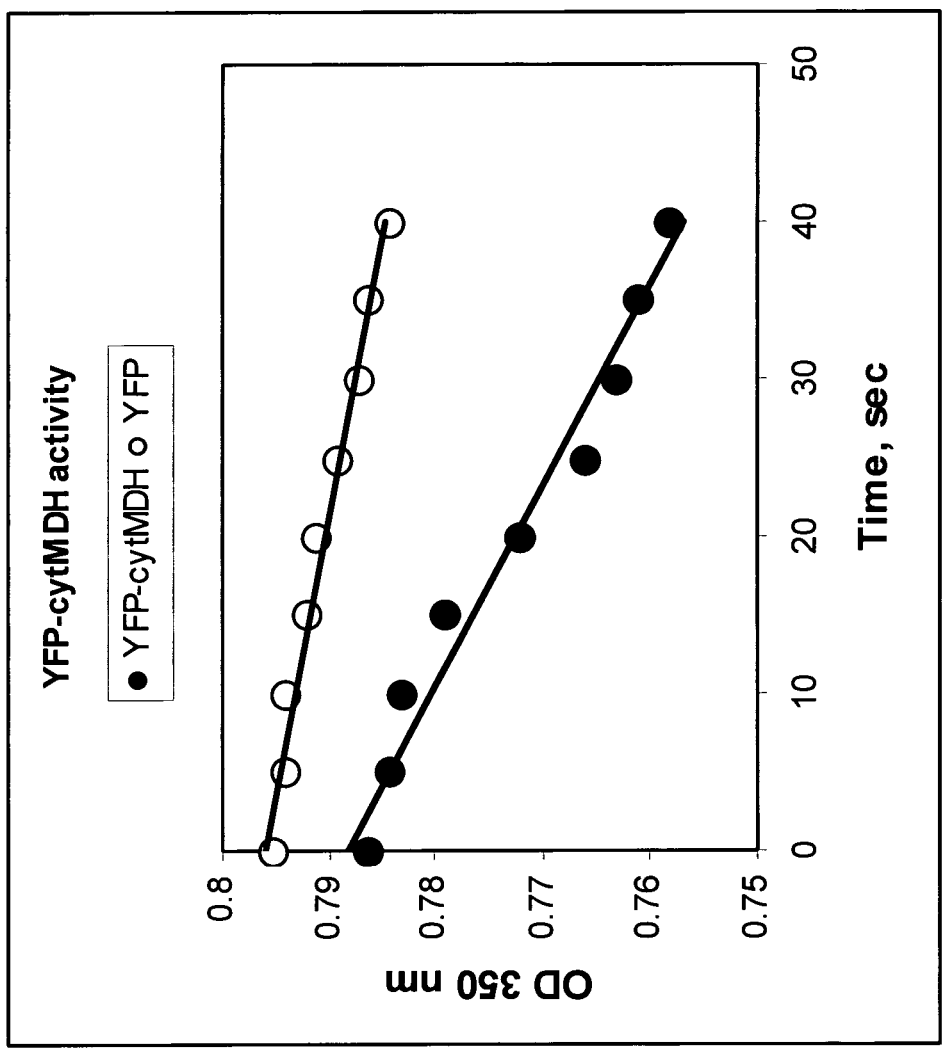
FIG. 4: MDH activity of the YFP-cytMDH construct. NSC-34 cells were transfected with YFP-MDH (black circles) or YFP (blank circles) expression plasmids. After 48 hours cells were lysed and aliquots containing 25 µg protein were removed for assessment of MDH activity as measured by the decrease in NADH (OD 340 nm) associated with conversion of oxaloacetate to malate.

The YFP-tagged cytMDH retained normal function. This was shown by measurement of MDH activity in naïve NSC-34 cells transfected with cytMDH-YFP (exogenous MDH) and YFP alone (endogenous MDH), which indicated an almost 3-fold increase in the rate of catalytic conversion of oxaloacetate to malate in cells transfected with the exogenous cytMDH (FIG. 4).

EXAMPLE 4

G93A-hSOD1 Upregulates cytMDH but Decreases in vivo cytMDH Activity

Figure 5A:
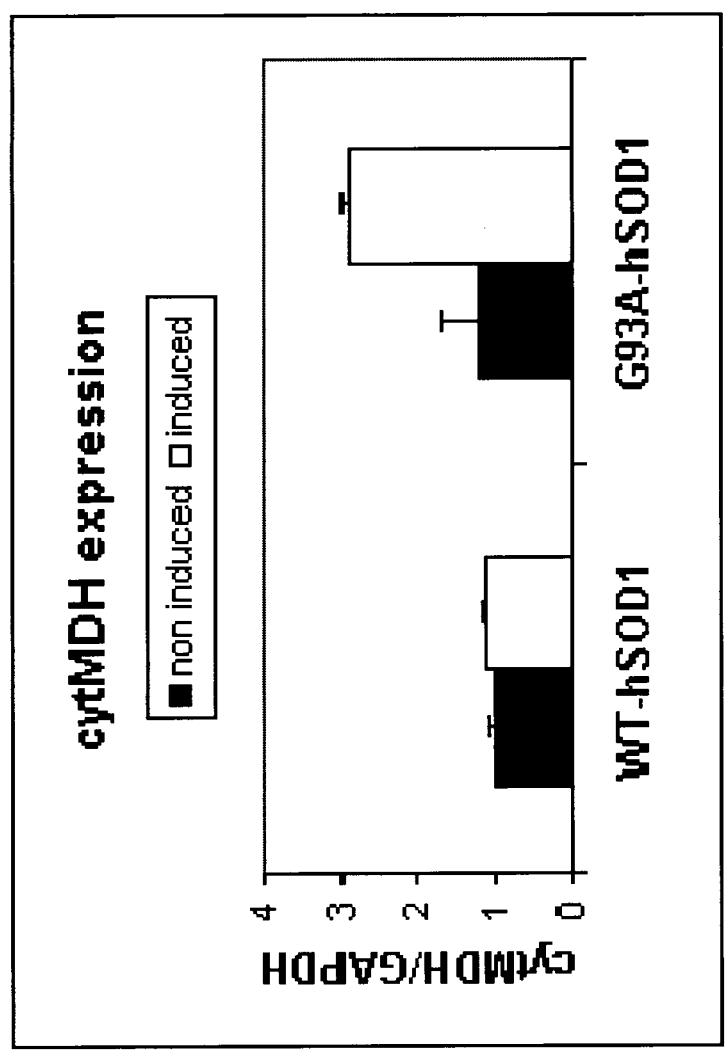
FIG. 5: WT-hSOD1-GFP and G93A-hSOD1-GFP cells were treated for 48 h with vehicle (non-induced) or doxycycline (induced) to induce hSOD1 expression. A) Expression of cytMDH was measured by RT-PCR relative to that of the housekeeping gene GAPDH. B) and C) MDH activity was measured in the non-induced and induced WT-hSOD1-GFP (B) and G93-A-hSOD1-GFP (C) cells. * indicates p<0.05 compared to non-induced control.
Figure 5B:
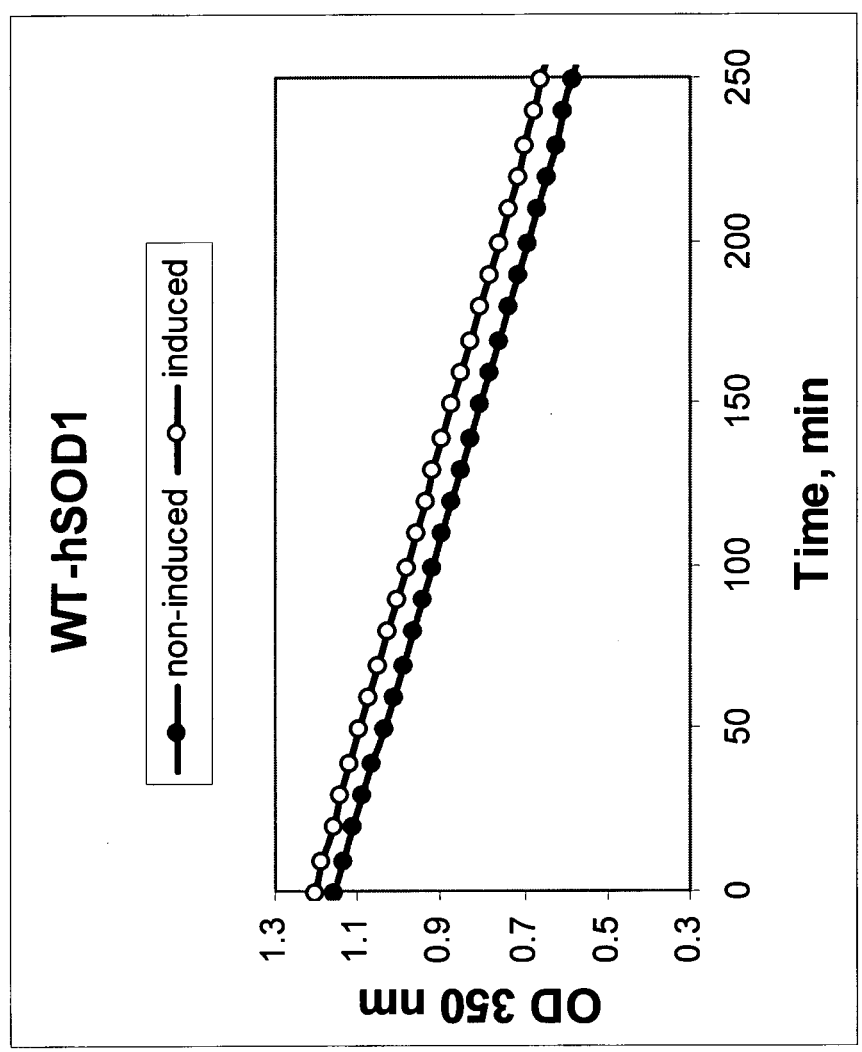
Figure 5C:
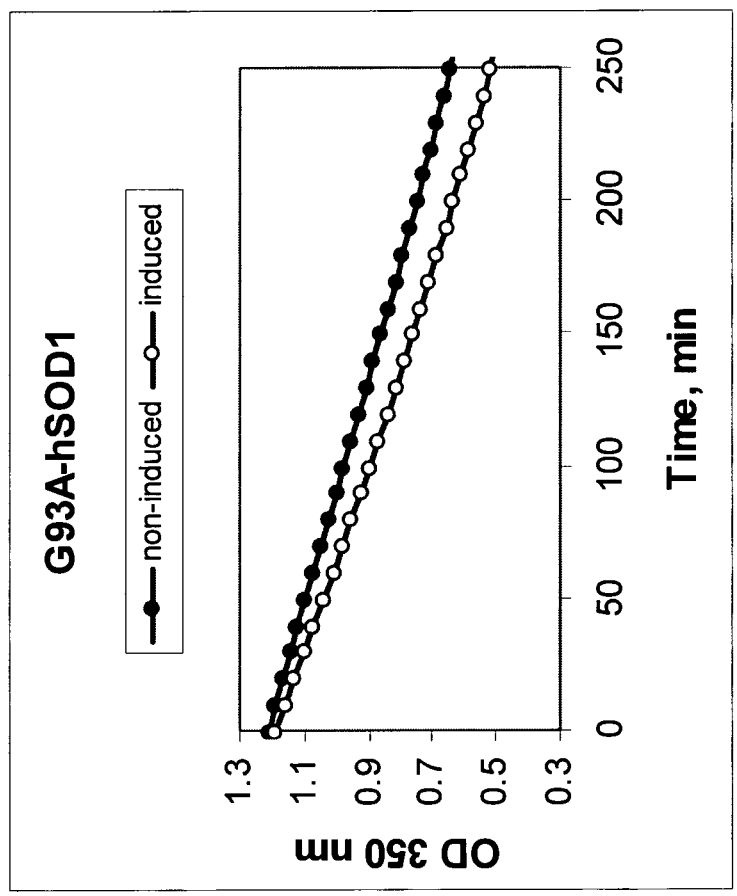

The impact of G93A-hSOD1-GFP and WT-hSOD1-GFP on expression of endogenous cytMDH was then assessed. Expression of endogenous cytMDH RNA in both G93A and WT hSOD1-GFP lines before and after doxycycline induction (to induce expression of the hSOD1-GFP proteins) is shown in FIG. 5. Significant 2.4-fold up-regulation of cyt-MDH mRNA was observed following 48 h of induction of expression of G93A-hSOD1-GFP, while no increase was found after induction of WT-hSOD1-GFP expression.

To evaluate whether endogenous cytMDH enzymatic activity is affected by the presence of G93A-hSOD1, endogenous cytMDH activity was assessed in vitro in lysates from cells of the lines stably containing the inducible G93A-hSOD1-GFP and WT-hSOD1-GFP with and without doxycycline treatment. The rate of conversion of oxaloacetate to malate in lysates of G93A-hSOD1-GFP cells was only slightly (10%) increased compared to non-induced cells. The respective cytMDH activity in non-induced WT-hSOD1-GFP cells was comparable to non-induced G93A-hSOD1-GFP cells and did not change after induction of WT-hSOD1 expression (FIG. 5).

Figure 6A:
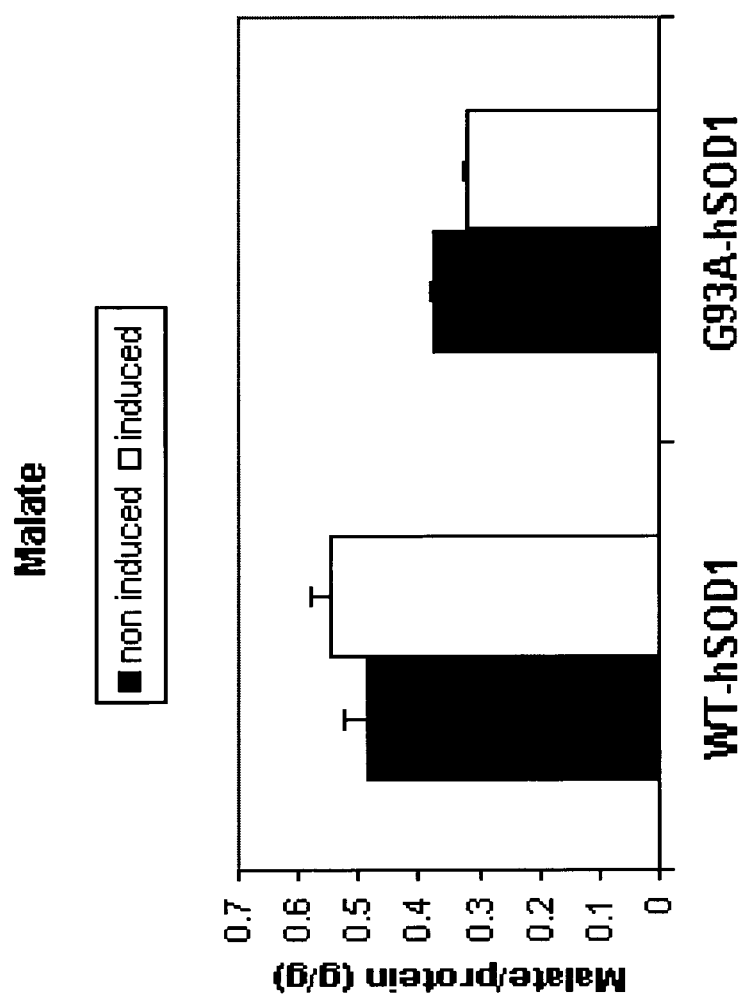
FIG. 6: WT-hSOD1-GFP and G93A-hSOD1-GFP cells were treated for 48 h with vehicle (non-induced) or doxycycline (induced) to induce hSOD1 expression. Malate (A) and Lactate (B) levels were assessed in solubilized cells and expressed in mg/mg cell protein. * indicates p<0.05 compared to non-induced control.
Figure 6B:
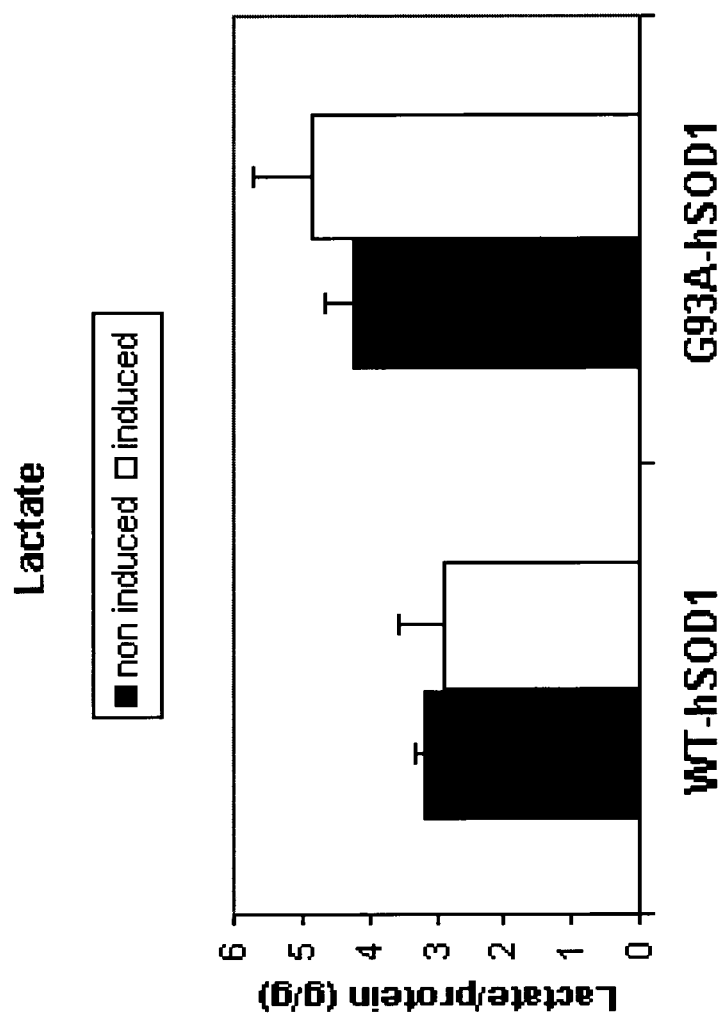

Cell lactate and malate levels were next measured to evaluate the impact of G93A-hSOD1 on cytMDH activity in intact cells. It was believed that if cytMDH activity was inhibited, conversion of oxaloacetate to malate will be inhibited and thus malate levels will decrease. In addition, conversion of NADH to NAD$^+$, which is coupled to this reaction, will thus occur through the alternative route, namely conversion of pyruvate to lactate, resulting in elevated lactate levels. Malate and lactate levels were thus assessed in stable lines expressing the inducible forms of G93A-hSOD1-GFP and WT-hSOD1-GFP. Malate and lactate levels measured in these cells without (non-induced) or with 48 hours of treatment with doxycycline are depicted in FIG. 6. Despite the increase in expression of the endogenous enzyme (FIG. 5), induction of expression of G93A-hSOD1-GFP resulted in a significant increase in lactate and decrease in malate levels. No such effect was seen with the WT-hSOD1-GFP expressing cells. Notably, even in the non-induced state, G93A-hSOD1-GFP cells had higher lactate and lower malate values compared to the cells expressing the WT-hSOD1-GFP cells.

Figure 7A:
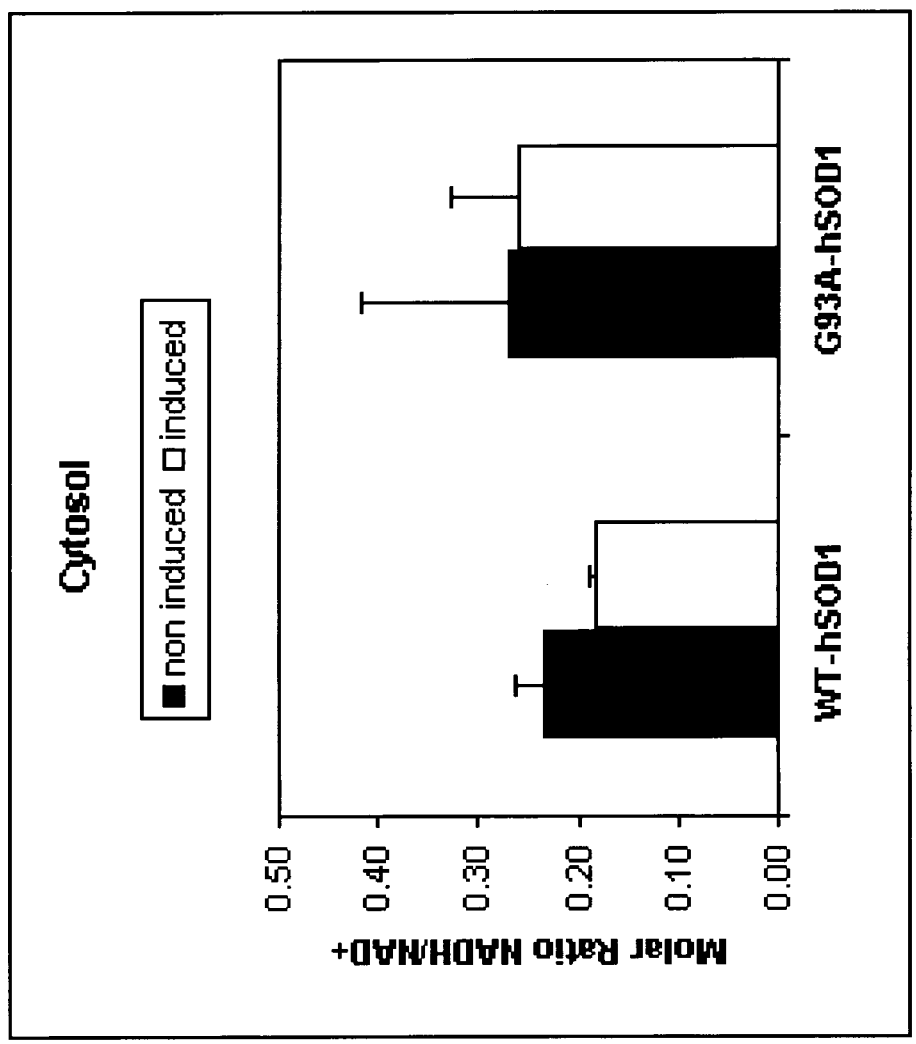
FIG. 7: WT-hSOD1-GFP and G93A-hSOD1-GFP cells were treated for 48 h with vehicle (non-induced) or doxycycline (induced) to induce hSOD1 expression. Cytosol (A) and mitochondrial (B) fractions were prepared and analyzed for $NAD^+$ and NADH contents. Results were normalized per protein content of the samples. ** indicates p<0.01 compared to non-induced control.
Figure 7B:
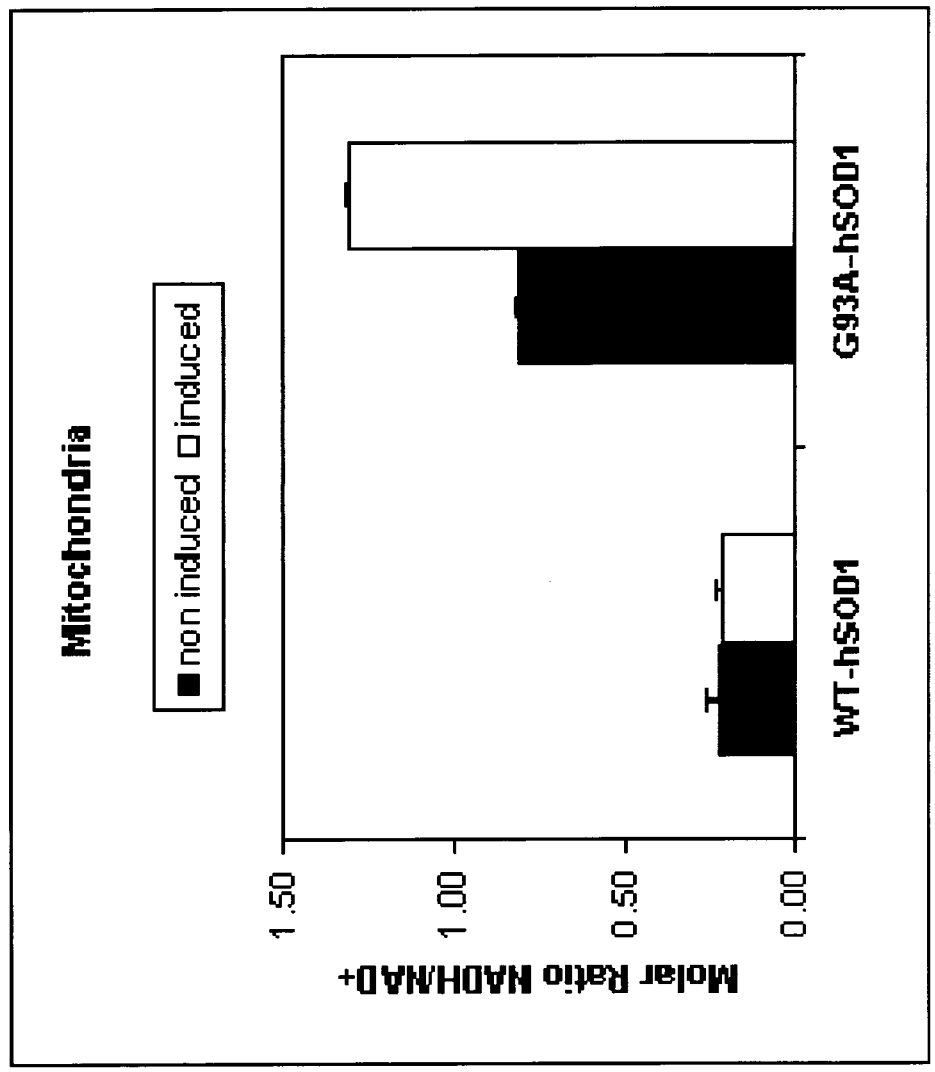

The effect of the change in efficiency of conversion of oxaloacetate to malate on NADH/NAD$^+$ ratio in the cytosol and mitochondria was assessed in both cell lines with and without hSOD1 induction (FIG. 7). There were no significant differences in NADH/NAD$^+$ in the cytosol between the non-induced G93A-hSOD1-GFP and WT-hSOD1-GFP cells. NADH/NAD$^+$ ratio in the cytosol did not differ in induced compared to non-induced G93A-hSOD1-GFP as well as WT-hSOD1-GFP cells. However, in the mitochondria, the NADH/NAD$^+$ ratio was significantly higher in the non-induced G93A-hSOD1-GFP than in the WT-hSOD1-GFP cells. A significant elevation in the mitochondrial NADH/NAD$^+$ ratio was found after a 48 hour-induction of expression of G93A-hSOD1-GFP but not of WT-hSOD1-GFP.

EXAMPLE 5

Identification of Peptide Agents that Inhibit the Formation of the Complex Between MDH1 and Mutant G93A-hSOD1

Figure 8:
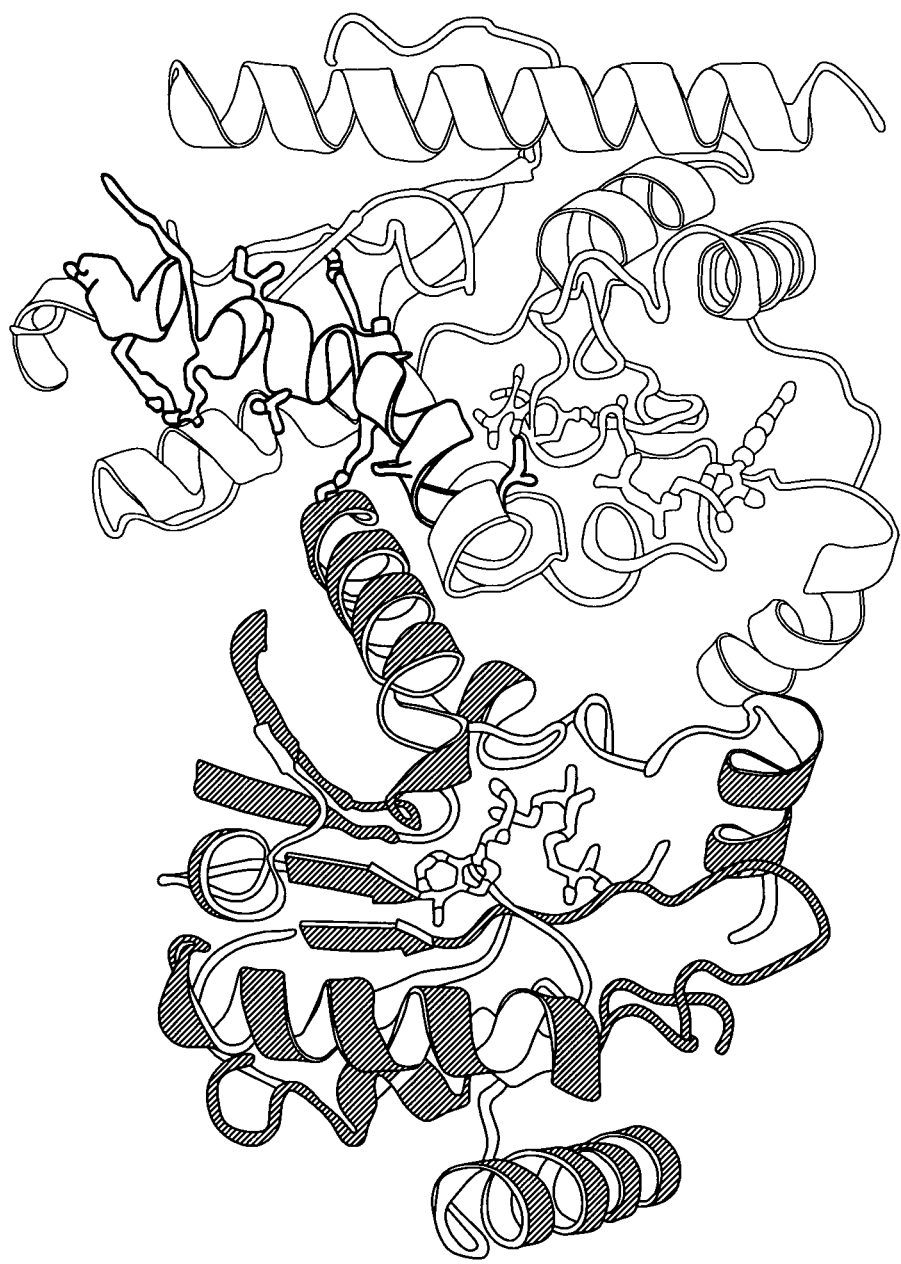
FIG. 8: Model of malate dehydrogenase. The identified peptide is highlighted in yellow, the monomeric units of MDH1 are in blue and green. NADH is represented in sticks and balls model.
Figure 9A:
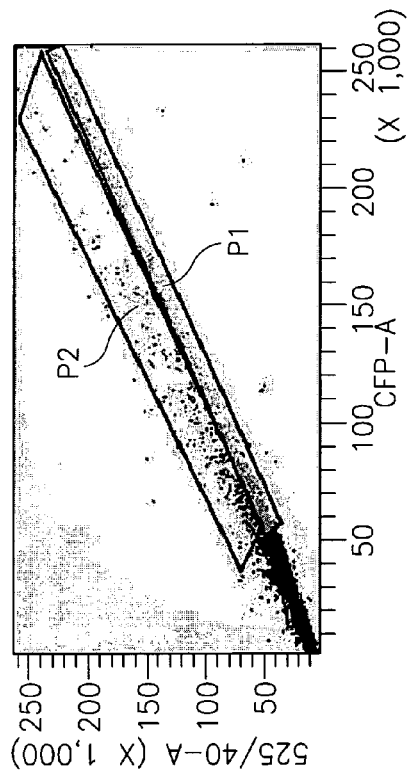
FIG. 9: FACS analysis of A) NSC-34 cells transfected with G93A-hSOD1-CFP plasmid and YFP-expressing plasmid (negative FRET control). B) NSC-34 cells transfected with G93A-hSOD1-CFP and cytMDH-YFP expression plasmids (positive FRET control). C) NSC-34 cells co-transfected with G93A-hSOD1-CFP/cytMDH-YFP expression plasmids and myc-tagged peptide 217-239 expression plasmids (negative FRET). D) NSC-34 cells co-transfected with G93A-hSOD1-CFP/cytMDH-YFP expression plasmids and myc-tagged peptide 14-27 expression plasmid (positive FRET). Excitation—405 nm, Emission—530 nm.
Figure 9B:
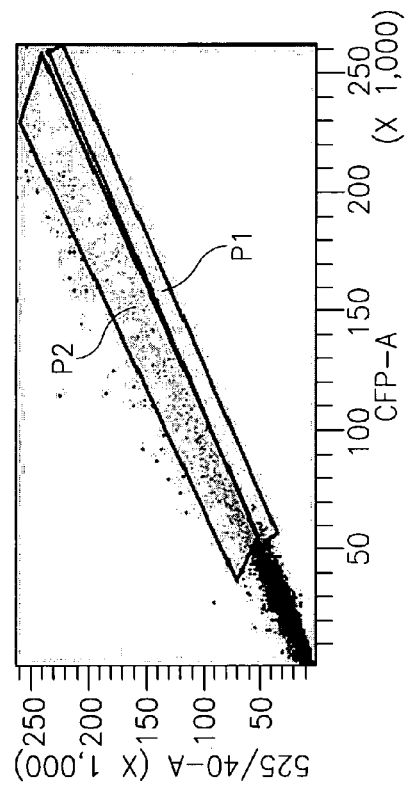
Figure 9C:
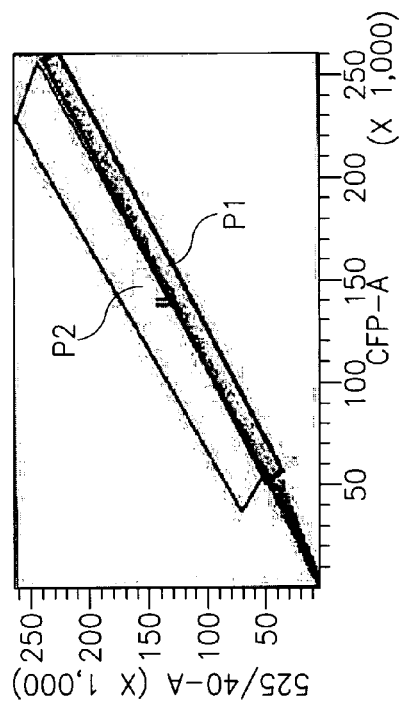
Figure 9D:
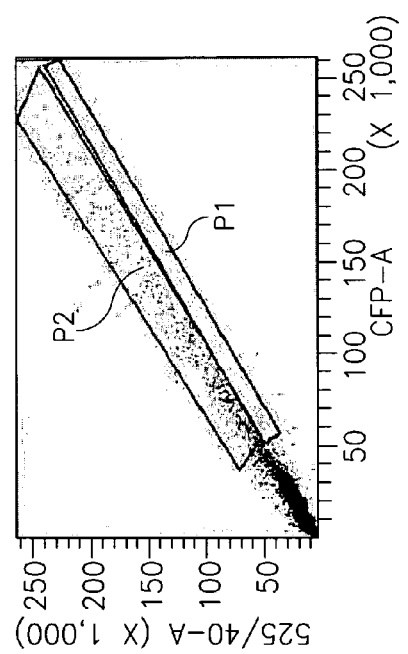

Four plasmids were shown to express peptides that interacted with SOD1. Of these, one corresponded to amino acids 14-27 of the cytMDH protein GQIAHSLLYSIGNG (SEQ ID No: 2) and three corresponded to amino acids 217-239 of the identified peptide corresponding to cytMDH protein SWLKGEFITTVQQRGAAVIKARK (SEQ ID NO: 1) (FIG. 8). The restriction map of MDH1 and the enzymes used for the library preparation are consistent with SEQ ID NO: 1 corresponding to nucleotides 745-807 in MDH1, namely the 66-nucleotide fragment 730-796.

The translated peptide, 217-239, having the sequence SWLKGEFITTVQQRGAAVIKARK (SEQ ID NO: 1), is located at the MDH1 surface, close to the MDH1 dimerization site (FIG. 8; peptide is highlighted in yellow, and monomeric units of MDH1 are in blue and green. NADH is represented in stick-and-ball model).

Ability of the 217-239 peptide to disrupt the G93A-hSOD1-cytMDH1 complex was tested by co-transfection into NSC-34 cells of constructs encoding myc-tagged 217-239 and the FRET-enabled G93A-hSOD1/cytMDH proteins, followed by FACS analysis to measure FRET. As shown in FIG. 9, the 217-239 peptide blocked FRET, indicating disruption of the G93A-hSOD1/cytMDH complex; compare (C) which contained the 217-239 peptide to (B) which lacked it. Cells transfected with constructs encoding G93A-hSOD1-CFP and YFP were utilized as the negative FRET control (A), while cells co-transfected with constructs encoding G93A-hSOD1-CFP/cytMDH-YFP and myc-tagged 14-27 peptide (D), found not to inhibit the interaction between the two proteins at 1:1:1 stoichiometry, served as a control for non-specific effects of the myc tag.

EXAMPLE 6

Figure 10A:
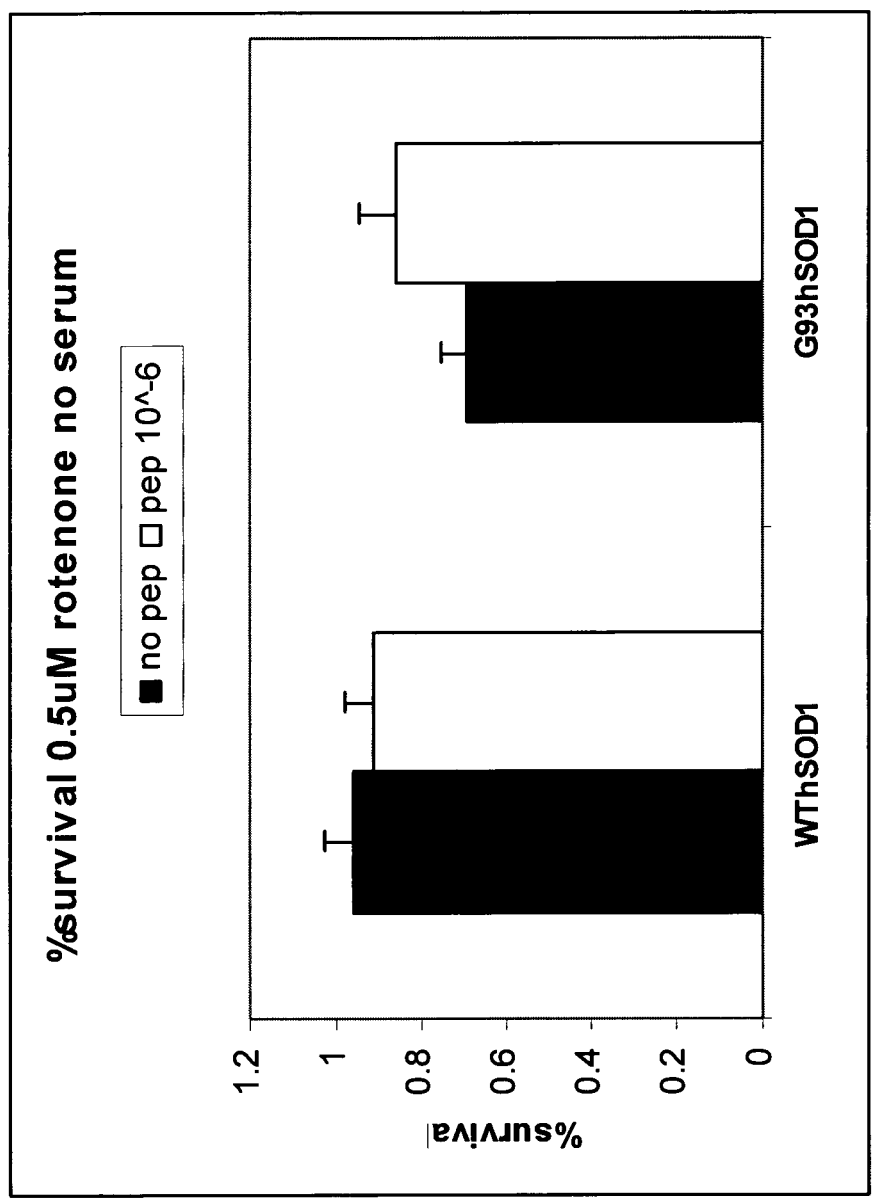
FIG. 10: Effect of peptide 217-239 on cell survival in rotenone-challenged WT-hSOD1-GFP- and G93A-hSOD1-GFP-expressing NSC-34 cells. Cells were incubated for 24 h with doxycycline and then for 4 hours with vehicle (solid bars) or 1 micromol/L peptide (hollow bars). A) 0.5 micromol/liter rotenone was added and incubation resumed for 24 hours. B) Medium was then replaced with DMEM containing 5% serum and 1 mg/ml glucose with vehicle (solid bars), and 1 micromol/L peptide (hollow bars) for 72 hours. Viability was assessed by the methylene blue assay. * indicates significant difference between levels in the presence and absence of peptide (t-test).
Figure 10B:
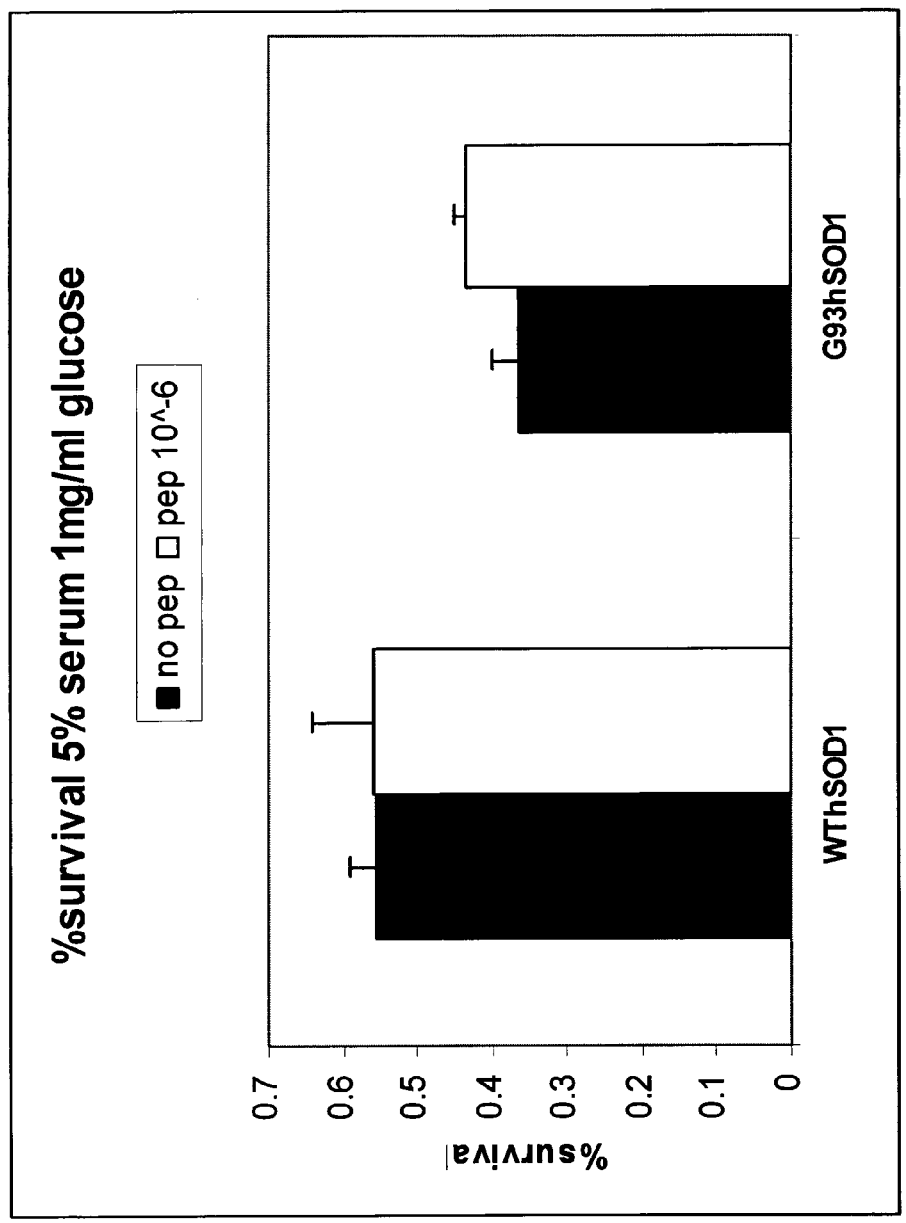

Inhibition of G93A-hSOD1-cytMDH Interaction Improves Cell Survival in the Presence of Rotenone Materials and Experimental Methods The SWLKGEFITTVQQRGAAVIKARK (SEQ ID NO: 1) peptide was synthesized (SBS Gentech Beijing) with 5,6-TAMRA modification (to allow detection) at the N-terminus, dissolved in 10% acetic acid, and diluted in cell culture medium containing 1% ethanol. Thus, 15,000 cells (WT-hSOD1 or G93A-hSOD1) seeded in each well of 96 wells plate in DMEM, 10% serum and doxycline (to induce expression of the hSOD1 proteins). 24 hours later, medium was replaced with serum free DMEM, and cells were incubated with 1 micromol/liter of the TAMRA-labeled SWLKGEFIT-TVQQRGAAVIKARK peptide or vehicle (1% acetic acid/ethanol) for 4 hours. In some experiments, 0.5 micromol/L rotenone was then added and incubation resumed for 24 hours (FIG. 10A). In other experiments, medium was replaced with low glucose (1 mg/ml) in DMEM with 5% serum with peptide or vehicle and incubation resumed for 72 hours (FIG. 10B). Cell survival was then assessed.

Results

The effect of the 217-239 peptide on cell death induced by the mitochondrial inhibitor rotenone on cells expressing WT-hSOD1-GFP and G93A-hSOD1-GFP was assessed. It was expected that, if G93A-hSOD1 causes cell death by gain-of-toxic-interaction, this should exacerbate rotenone-induced death, and the exacerbation should be alleviated by inhibiting this interaction with the 217-239 peptide.

Expression of WT-hSOD1 or G93A-hSOD1 cells was induced with doxycline, after which medium was replaced with serum-free DMEM, and cells were incubated with 1 micromol/liter of TAMRA-SWLKGEFITTVQQRGAA-VIKARK peptide or vehicle (1% acetic acid/ethanol), followed by addition of rotenone. Treatment with rotenone reduced cell viability to a greater extent in G93A-hSOD1-GFP than WT-hSOD1-GFP cells as measured by methylene blue assay (relative to the survival without rotenone). In the presence of the 217-239 peptide, the effects of rotenone were greatly diminished in the G93A-hSOD1-GFP but not non-induced WT-hSOD1-GFP lines (FIG. 10A).

In other experiments, addition of peptide was followed by replacement of the media with low glucose (1 mg/ml) DMEM with 5% serum with peptide or vehicle. Low glucose levels reduced cell viability to a greater extent in G93A-hSOD1-GFP than WT-hSOD1-GFP cells, as measured by methylene blue assay (relative to the survival with normal glucose). In the presence of the 217-239 peptide, the effects of low glucose were significantly diminished in the G93A-hSOD1 but not non-induced WT-hSOD1 cell lines (FIG. 10B).

These findings show that inhibition of G93A-hSOD1-cytMDH interaction improves cell survival by inhibiting gain of this toxic interaction.

EXAMPLE 7

Figure 11:
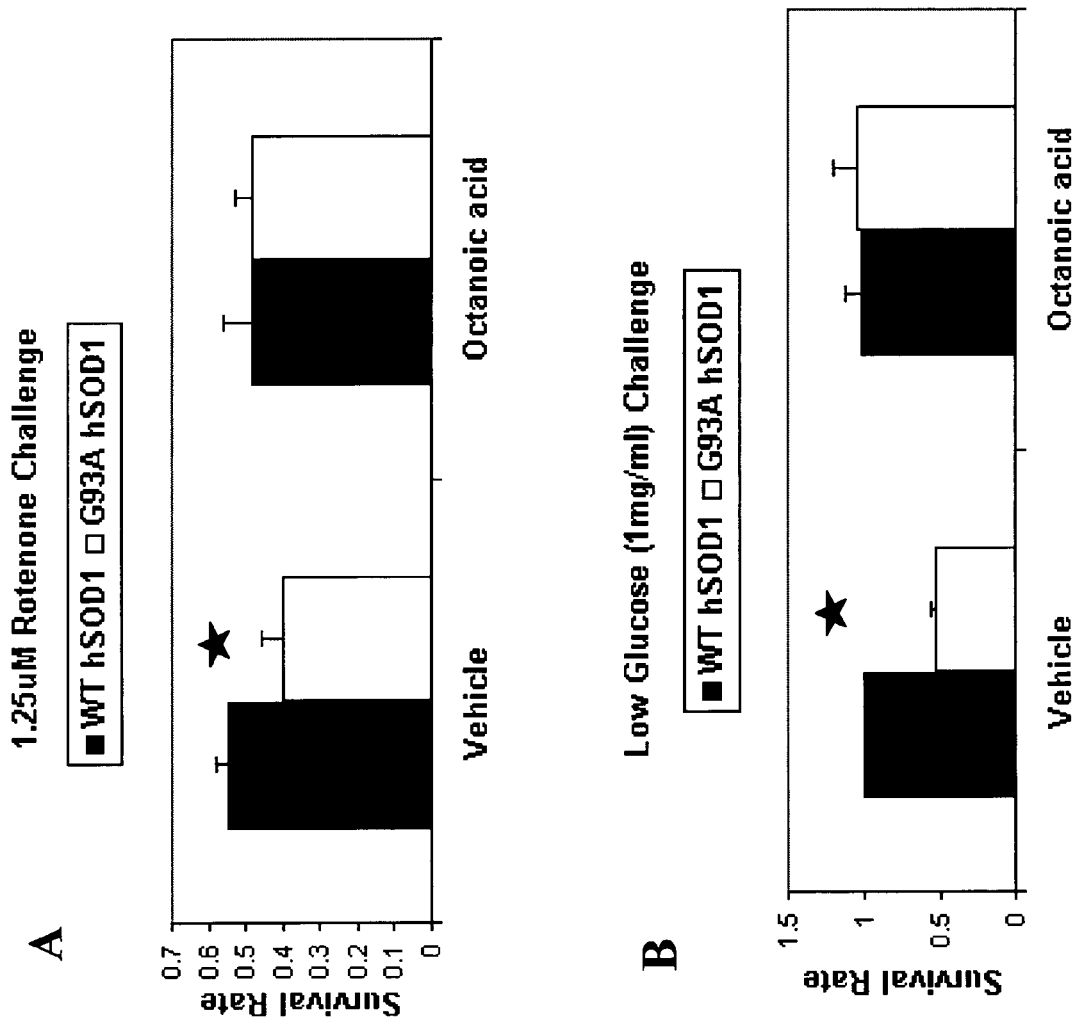
FIG. 11: Effects of octanoic acid on cell survival in rotenone-challenged WT-hSOD1-GFP- and G93A-hSOD1-GFP-expressing NSC-34 cells. A) Cells were incubated for 24 h with doxycycline and then for (i) 24 hours in the presence of rotenone (1.25 micromol/liter)+vehicle (solid bars), or (ii) rotenone+3 mM octanoic acid (hollow bars). B) Cells were incubated with 3 mM octanoic acid or vehicle and medium replaced with low (1 mg/ml) glucose in DMEM with 5% serum for 72 hours. Cell survival was then assessed. Viability was assessed by methylene blue assay. * indicates significant difference between wild-type and mutant cell levels (t-test).

Gain of Toxic Interaction of G93A SOD1-GFP is Due to Inhibition of the Malate-Aspartate Shuttle The effects of octanoic acid on survival of rotenone- and low glucose challenged cells expressing WT-hSOD1-GFP and G93A-hSOD1-GFP were assessed (FIG. 11). Treatment with rotenone (1.25 micromol/liter for 24 h) reduced cell viability to a greater extent in G93A-hSOD1-GFP than WT-hSOD1-GFP expressing cells as measured by methylene blue assay (relative to the survival without rotenone). In the presence of octanoic acid, the effects of rotenone were greatly diminished in the G93A-hSOD1-GFP but not non-induced WT-hSOD1-GFP lines (FIG. 11A). Low glucose levels resulted in reduced cell viability to a greater extent in G93A-hSOD1-GFP than WT-hSOD1-GFP cells as measured by methylene blue assay (relative to the survival with normal glucose). In the presence of octanoic acid, the effects of low glucose were greatly diminished in the G93A-hSOD1-GFP but not non-induced WT-hSOD1-GFP lines (FIG. 11B). Thus, gain of toxic interaction of G93A SOD1-GFP is due to inhibition of the malate-aspartate shuttle.

As provided herein, an interaction was identified, using novel FRET techniques in live motor-neuron derived cells, between mutant hSOD1-GFP (disease protein) and BFP-tagged cytMDH, which does not occur with the wild type hSOD1-GFP. Furthermore, using confocal microscopy close proximity was demonstrated between these proteins using a different pair of fluorophores and transient transfection into the parent NSC-34 cell line. Further interaction was demonstrated between BFP-tagged cytMDH and untagged mutant hSOD1, which does not occur with untagged WT-hSOD1 in the cells using pull-down immunoprecipitation techniques. The tagged cytMDH retained MDH enzymatic activity, showing that its conformation was largely normal. Moreover, expression of the mutant protein affected expression of endogenous cytMDH (increase) and the levels of cell malate (decrease) and lactate (increase) as well as the NADH/NAD$^+$ ratio in the mitochondria (increase), all of which are compatible with the consequences of inhibition of endogenous cytMDH by G93A-hSOD1 and are not seen with the WT-hSOD1.

Malate dehydrogenases (MDH, L-malate:NAD oxidoreductase, EC 1.1.1.37), catalyze the NAD/NADH-dependent interconversion of malate and oxaloacetate in the cytoplasm (cytMDH) and mitochondria (MitMDH). This reaction plays a key part in the malate/aspartate shuttle between the cytoplasm across the mitochondrial membrane, and in the tricarboxylic acid cycle within the mitochondrial matrix. The association between the mutant hSOD1 with cytMDH may rely on structural properties of these proteins and imply that some structural properties of the mutant hSOD1 differ from those of the wild-type enzyme. This notion is compatible with the formation of aggregates and inclusion bodies by the mutant but not WT protein (3,17). Cytosolic MDH and mitMDH share a common catalytic mechanism and their kinetic properties are similar, which demonstrates a high degree of structural similarity (3). The specificity of the interaction between G93A-hSOD1 and cytMDH may thus be due to the preferential cytoplasmic localization of both.

Cytosolic MDH is a key enzyme in the malate-aspartate shuttle which is considered the most important shuttle in the brain and is particularly important in neurons. The malate-aspartate shuttle and the glycerol phosphate shuttle act to transfer reducing equivalents from NADH in the cytosol to the mitochondria, since the inner mitochondrial membrane is impermeable to NADH and NAD$^+$ (18). Thus, in the cytoplasm, cytMDH converts oxaloacetate to malate, at the same time reoxidizing NADH in the cytosol to NAD$^+$. Malate then enters the mitochondria in exchange for α-ketoglutarate. Mitochondrial MDH, which is part of the tricarboxylic acids (TCA) cycle enzyme, converts malate to oxaloacetate, at the same time reducing NAD$^+$, forming equivalent amounts of NADH. This transfer of reducing equivalents is essential for maintaining a favorable NAD$^+$/NADH ratio required for the oxidative metabolism of glucose and synthesis of neurotransmitters in brain. Inhibition of this shuttle thus impairs the utilization of glucose, which is a main source of metabolic energy in the neurons favoring the anaerobic option (formation of lactate) over the aerobic option (TCA cycle) and resulting in a lower ATP yield. Inhibition of the malate-aspartate shuttle has been shown to reduce consumption of oxygen in porcine carotid arterial strips (19), thus leading to ischemic conditions in the cells which are associated with increase in anaerobic conversion of pyruvate to lactate. Under such conditions, oxidative metabolism of pyruvate via the tricarboxylic acid (TCA) cycle, which would be more efficient in terms of ATP production, is diminished (18). Ischemic conditions increase mitochondrial NADH/NAD$^+$ ratio (20). The results of the studies presented herein are compatible with inhibition of cytMDH and consequently the malate-aspartate shuttle in cells expressing the mutant hSOD1. Thus, malate levels decreased while lactate levels increased, confirming anaerobic conditions, and the mitochondrial NADH/NAD$^+$ ratio increased accordingly. By this route, interaction between G93A-hSOD1 and cyt-MDH may reduce the maximal energy exploitation by the TCA cycle, thus shifting the cell towards anaerobic respiration and a state of hypoxia.

Another implication of inhibition of the malate-aspartate shuttle is an increase in reactive oxygen species (ROS) in mutant hSOD-expressing cells. The activity of α-Ketoglutarate dehydrogenase (α-KGDH), one of the key enzymes in the TCA cycle, is regulated by the NADH/NAD$^+$ ratio. A higher NADH/NAD$^+$ ratio induces a higher rate of $H_2O_2$ production by the enzyme. The observed increase in NADH/NAD$^+$ ratio may thus promote α-KGDH-mediated ROS production (21). Increase in ROS has been shown to induce MDH expression (22). The up-regulation of cytMDH expression shown here in G93A-hSOD1-expressing cells is thus consistent with elevated ROS in the cells. The fact that, despite upregulation of cytMDH expression, enzymatic activity was only slightly enhanced in these cells is compatible with inhibition of the enzyme activity by the mutant hSOD1 protein.

It is interesting to note that even the non-induced G93A-hSOD1 cells had significantly higher levels of lactate and mitochondrial NADH/NAD+ ratio compared to the respective values in WT-hSOD1 cells. As with most inducible systems, there was about 10% leakage in expression of the mutant protein in the non-induced cells. Recent studies indicated that a low level of G93A-hSOD1 was sufficient to increase the production of ROS and to cause mitochondrial damage and death in NSC-34 cells (4). We thus assume that even a slight leak into expression of the inducible plasmid is sufficient to elicit some state of hypoxia in the G93A-hSOD1 cells.

Thus, the interaction between the mutant G93A-hSOD1 protein with cytMDH may result in inhibition of the malate-aspartate shuttle, leading to increased NADH/NAD$^+$ ratio in the mitochondria. The latter results in inhibition of α-KGDH and elevates deleterious ROS production. Increase in ROS may inhibit the activity of HIF-1α-prolyl-4-hydroxylases (PHD) which acts to enhance the degradation of hypoxia induced factor 1α (23). In addition, a decrease in the cytosolic PHD substrate α-Ketoglutarate might also lead to a decrease in PHD activity, resulting in an increase in HIF-1α. On the other hand, HIF-1α induces PHD expression thereby promoting its own degradation (24). Indeed, previous studies have demonstrated that neurons expressing G93A-hSOD1 are in a chronic state of hypoxia, as demonstrated in HIF-1α upregulation and the impaired hypoxia response in these cells (Mali & Zisapel unpublished). Thus, inhibition of the malate aspartate shuttle may, via modulation of PHD enzymatic activity, explain the dysregulation of cellular responses to hypoxia in the G93A-hSOD1 expressing cells.

Another aspect of impaired malate-aspartate shuttle is the impairment in synthesis of neurotransmitters, particularly glutamate. The cytosolic aspartate aminotransferase converts aspartate to oxaloacetate, while simultaneously converting α-ketoglutarate into glutamate Inhibition of the malate-aspartate shuttle significantly decreased the biosynthesis of neurotransmitter glutamate in synaptosomes (28). Abnormal glutamate metabolism has also been reported in ALS. Reduced glutamate levels have been reported in brain and spinal cord tissue of ALS patients (29). Glutamate dehydrogenase activity, which converts α-ketoglutarate to glutamate, was found to be decreased in leukocytes from ALS patients (30).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

1. Carri, M. T., Ferri, A., Battistoni, A., Famhy, L., Gabbianelli, R., Poccia, F., and Rotilio, G. (1997) FEBS Lett 414, 365-368
2. Kruman, II, Pedersen, W. A., Springer, J. E., and Mattson, M. P. (1999) Exp Neurol 160, 28-39
3. Menzies, F. M., Cookson, M. R., Taylor, R. W., Turnbull, D. M., Chrzanowska-Lightowlers, Z. M., Dong, L., Figlewicz, D. A., and Shaw, P. J. (2002) Brain 125, 1522-1533
4. Rizzardini, M., Mangolini, A., Lupi, M., Ubezio, P., Bendotti, C., and Cantoni, L. (2005) J Neurol Sci 232, 95-103
5. Beal, M. F. (2000) Brain 123 (Pt 7), 1291-1292
6. Bendotti, C., and Carri, M. T. (2004) Trends Mol Med 10, 393-400
7. Lambrechts, D., Storkebaum, E., Morimoto, M., Del-Favero, J., Desmet, F., Marklund, S. L., Wyns, S., Thijs, V., Andersson, J., van Marion, I., Al-Chalabi, A., Bornes, S., Musson, R., Hansen, V., Beckman, L., Adolfsson, R., Pall, H. S., Prats, H., Vermeire, S., Rutgeerts, P., Katayama, S., Awata, T., Leigh, N., Lang-Lazdunski, L., Dewerchin, M., Shaw, C., Moons, L., Vlietinck, R., Morrison, K. E., Robberecht, W., Van Broeckhoven, C., Collen, D., Andersen, P. M., and Carmeliet, P. (2003) Nat Genet 34, 383-394
8. Greenway, M. J., Andersen, P. M., Russ, C., Ennis, S., Cashman, S., Donaghy, C., Patterson, V., Swingler, R., Kieran, D., Prehn, J., Morrison, K. E., Green, A., Acharya, K. R., Brown, R. H., Jr., and Hardiman, O. (2006) Nat Genet 38, 411-413
9. Brockington, A., Wharton, S. B., Fernando, M., Gelsthorpe, C. H., Baxter, L., Ince, P. G., Lewis, C. E., and Shaw, P. J. (2006) J Neuropathol Exp Neurol 65, 26-36
10. Bruijn, L. I., Miller, T. M., and Cleveland, D. W. (2004) Annu Rev Neurosci 27, 723-749
11. Zhang, F., Strom, A. L., Fukada, K., Lee, S., Hayward, L. J., and Zhu, H. (2007) J Biol Chem
12. Chan, F. K. (2004) Methods Mol Biol 261, 371-382
13. Cashman, N. R., Durham, H. D., Blusztajn, J. K., Oda, K., Tabira, T., Shaw, I. T., Dahrouge, S., and Antel, J. P. (1992) Dev Dyn 194, 209-221
14. Zheng, J., Varnum, M. D., and Zagotta, W. N. (2003) J Neurosci 23, 8167-8175
15. Bubis, M., and Zisapel, N. (1998) Mol Cell Endocrinol 137, 59-67
16. Shinder, G. A., Lacourse, M. C., Minotti, S., and Durham, H. D. (2001) J Biol Chem 276, 12791-12796
17. Takeuchi, H., Kobayashi, Y., Ishigaki, S., Doyu, M., and Sobue, G. (2002) J Biol Chem 277, 50966-50972
18. McKenna, M. C., Waagepetersen, H. S., Schousboe, A., and Sonnewald, U. (2006) Biochem Pharmacol 71, 399-407
19. Barron, J. T., Gu, L., and Parrillo, J. E. (1998) J Mol Cell Cardiol 30, 1571-1579
20. Zhou, L., Stanley, W. C., Saidel, G. M., Yu, X., and Cabrera, M. E. (2005) J Physiol 569, 925-937
21. Adam-Vizi, V. (2005) Antioxid Redox Signal 7, 1140-1149
22. Hu, R., Jin, H., Zhou, S., Yang, P., and Li, X. (2007) Placenta 28, 399-407
23. Pan, Y., Mansfield, K. D., Bertozzi, C. C., Rudenko, V., Chan, D. A., Giaccia, A. J., and Simon, M. C. (2006) Mol Cell Biol
24. Marxsen, J. H., Stengel, P., Doege, K., Heikkinen, P., Jokilehto, T., Wagner, T., Jelkmann, W., Jaakkola, P., and Metzen, E. (2004) Biochem J 381, 761-767
25. Siciliano, G., Piazza, S., Carlesi, C., Del Corona, A., Franzini, M., Pompella, A., Malvaldi, G., Mancuso, M., Paolicchi, A., and Murri, L. (2007) J Neurol
26. Lederer, C. W., Torrisi, A., Pantelidou, M., Santama, N., and Cavallaro, S. (2007) BMC Genomics 8, 26
27. Fergani, A., Oudart, H., Gonzalez de Aguilar, J. L., Fricker, B., Rene, F., Hocquette, J. F., Meininger, V., Dupuis, L., and Loeffler, J. P. (2007) J Lipid Res
28. Palaiologos, G., Hertz, L., and Schousboe, A. (1988) J Neurochem 51, 317-320
29. Plaitakis, A., Constantakakis, E., and Smith, J. (1988) Ann Neurol 24, 446-449
30. Hugon, J., Tabaraud, F., Rigaud, M., Vallat, J. M., and Dumas, M. (1989) Neurology 39, 956-958
31. Van Westerlaak, M. G., Joosten, E. A., Gribnau, A. A., Cools, A. R., and Bar, P. R. (2001) Brain Res 922, 243-249
32. Kaal, E. C., Vlug, A. S., Versleijen, M. W., Kuilman, M., Joosten, E. A., and Bar, P. R. (2000) J Neurochem 74, 1158-1165
33. Ramos, M., del Arco, A., Pardo, B., Martinez-Serrano, A., Martinez-Morales, J. R., Kobayashi, K., Yasuda, T., Bogonez, E., Bovolenta, P., Saheki, T., and Satrustegui, J. (2003) Brain Res Dev Brain Res 143, 33-46

The invention claimed is:

1. A recombinant or synthetic peptide agent consisting of the sequence SWLKGEFITTVQQRGAAVIKARK (SEQ ID NO: 1).

2. A pharmaceutical composition comprising (a) a pharmaceutically acceptable carrier and (b) as an active ingredient, a recombinant or synthetic peptide agent consisting of the sequence SWLKGEFITTVQQRGAAVIKARK (SEQ ID NO: 1).

* * * * *

```
SEQUENCE LISTING

<160> NUMBER OF SEQ ID NOS: 15

<210> SEQ ID NO 1
<211> LENGTH: 23
<212> TYPE: PRT
<213> ORGANISM: Mus musculus

<400> SEQUENCE: 1

Ser Trp Leu Lys Gly Glu Phe Ile Thr Thr Val Gln Gln Arg Gly Ala
1               5                   10                  15

Ala Val Ile Lys Ala Arg Lys
            20

<210> SEQ ID NO 2
<211> LENGTH: 14
<212> TYPE: PRT
<213> ORGANISM: Mus musculus

<400> SEQUENCE: 2

Gly Gln Ile Ala His Ser Leu Leu Tyr Ser Ile Gly Asn Gly
1               5                   10

<210> SEQ ID NO 3
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 3
cctagcggcc gcaagcagtg gtatcaacgc agagt                         35
```

<210> SEQ ID NO 4
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 4
cattacctgt ccacacaatc tgccc					25

<210> SEQ ID NO 5
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 5
cacctactca gacaatgcga tgc					23

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
ctcagatatc gatctcaagc t					21

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
cctctacaaa tgtggtatgg ctg					23

<210> SEQ ID NO 8
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 8
cattacctgt ccacacaatc tgccc					25

<210> SEQ ID NO 9
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 9
cacctactca gacaatgcga tgc					23

<210> SEQ ID NO 10
<211> LENGTH: 23
<212> TYPE: DNA
<213> ORGANISM: Artificial Sequence
<220> FEATURE:
<223> OTHER INFORMATION: synthetic oligonucleotide

```
<400> SEQUENCE: 10
aattctgcga tatcgcggcc gcg                                    23

<210> SEQ ID NO 11
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 11
gatccgcggc gcgatatcg ca                                      22

<210> SEQ ID NO 12
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 12
aattctgccg atatcgcggc cgcg                                   24

<210> SEQ ID NO 13
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 13
gatccgcggc cgcgatatcg gca                                    23

<210> SEQ ID NO 14
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 14
aattctgccc gatacgcggc cgcg                                   24

<210> SEQ ID NO 15
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 15
gatccgcggc cgcgatatcg ggca                                   24
```